(12) United States Patent  
Burkholz et al.

(10) Patent No.: US 8,377,040 B2  
(45) Date of Patent: Feb. 19, 2013

(54) EXTRAVASCULAR SYSTEM VENTING

(75) Inventors: Jonathan Karl Burkholz, Salt Lake City, UT (US); Wade A. Powell, Draper, UT (US); Jason Hillman, West Jordan, UT (US); Weston F. Harding, Lehi, UT (US); Kelly D. Christensen, Centerville, UT (US); John Stokes, Ogden, UT (US); Marty L. Stout, South Weber, UT (US); Christopher N. Cindrich, Draper, UT (US); Dinesh S. Kommireddy, Mdivale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 719 days.

(21) Appl. No.: 11/935,057

(22) Filed: Nov. 5, 2007  
(Under 37 CFR 1.47)

(65) Prior Publication Data

US 2008/0287906 A1  Nov. 20, 2008

Related U.S. Application Data

(60) Provisional application No. 60/864,505, filed on Nov. 6, 2006.

(51) Int. Cl.  
*A61M 25/16*  (2006.01)

(52) U.S. Cl. ........................................ 604/533; 604/122

(58) Field of Classification Search .................. 604/122, 604/126, 533–536, 539, 45, 167.02  
See application file for complete search history.

(56) References Cited

U.S. PATENT DOCUMENTS

| | | | |
|---|---|---|---|
| 4,003,403 A | 1/1977 | Nehring | |
| 4,193,399 A | 3/1980 | Robinson | |
| 4,269,186 A | 5/1981 | Loveless et al. | |
| 4,682,980 A | 7/1987 | Suzuki | |
| 4,765,588 A | 8/1988 | Atkinson | |
| 4,894,052 A | 1/1990 | Crawford | |
| 4,917,671 A | 4/1990 | Chang | |
| 4,935,010 A * | 6/1990 | Cox et al. ....................... | 604/122 |
| 5,032,116 A | 7/1991 | Peterson et al. | |
| 5,226,883 A | 7/1993 | Katsaros et al. | |
| 5,242,411 A | 9/1993 | Yamamoto et al. | |
| 5,251,873 A | 10/1993 | Atkinson et al. | |
| 5,295,657 A | 3/1994 | Atkinson | |
| 5,295,658 A | 3/1994 | Atkinson et al. | |
| 5,295,970 A | 3/1994 | Clinton et al. | |
| 5,338,313 A | 8/1994 | Mollenauer et al. | |
| 5,342,316 A | 8/1994 | Wallace | |
| 5,417,664 A | 5/1995 | Felix et al. | |
| 5,441,487 A | 8/1995 | Vedder | |
| 5,474,544 A | 12/1995 | Lynn | |
| 5,501,426 A | 3/1996 | Atkinson et al. | |
| 5,501,671 A | 3/1996 | Rosen et al. | |
| 5,533,708 A | 7/1996 | Atkinson et al. | |
| 5,542,932 A | 8/1996 | Daugherty | |
| 5,549,651 A | 8/1996 | Lynn | |
| 5,919,160 A | 7/1999 | Sanfilippo, II | |
| 5,954,657 A | 9/1999 | Rados | |

(Continued)

*Primary Examiner* — Kevin C Sirmons  
*Assistant Examiner* — Phillip Gray  
(74) *Attorney, Agent, or Firm* — Jeanne Lukasavage; Craig Metcalf; Kirton McConkie

(57) ABSTRACT

A vascular access device may form part of an extravascular system and function as an adapter including a gas permeable vent. A method of venting a medical device may include providing a vascular access device as part of an extravascular system, providing a gas permeable vent within the vascular access device, venting gas from the system through the vent, and closing the vent.

7 Claims, 24 Drawing Sheets

U.S. PATENT DOCUMENTS

| | | |
|---|---|---|
| 5,957,898 A | 9/1999 | Jepson et al. |
| 6,139,534 A | 10/2000 | Niedospial, Jr. et al. |
| 6,171,287 B1 | 1/2001 | Lynn et al. |
| 6,261,282 B1 | 7/2001 | Jepson et al. |
| 6,344,033 B1 | 2/2002 | Jepson et al. |
| 6,503,225 B1 | 1/2003 | Kirsch et al. |
| 6,595,964 B2 | 7/2003 | Finley et al. |
| 6,651,956 B2 | 11/2003 | Miller |
| 6,669,681 B2 | 12/2003 | Jepson et al. |
| 6,866,656 B2 | 3/2005 | Tingey et al. |
| 6,908,459 B2 | 6/2005 | Harding et al. |
| 2002/0193752 A1 | 12/2002 | Lynn |
| 2005/0027256 A1* | 2/2005 | Barker et al. ............ 604/164.12 |
| 2005/0077225 A1 | 4/2005 | Usher et al. |
| 2005/0256457 A1 | 11/2005 | Rome |
| 2005/0256500 A1 | 11/2005 | Fujii |

* cited by examiner

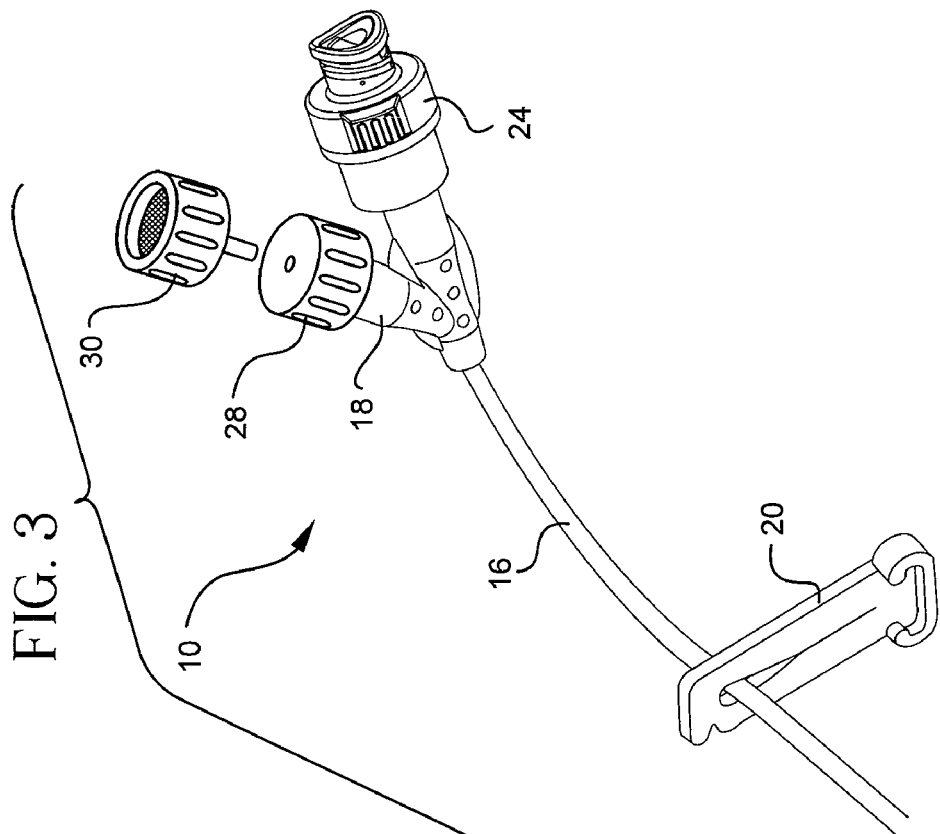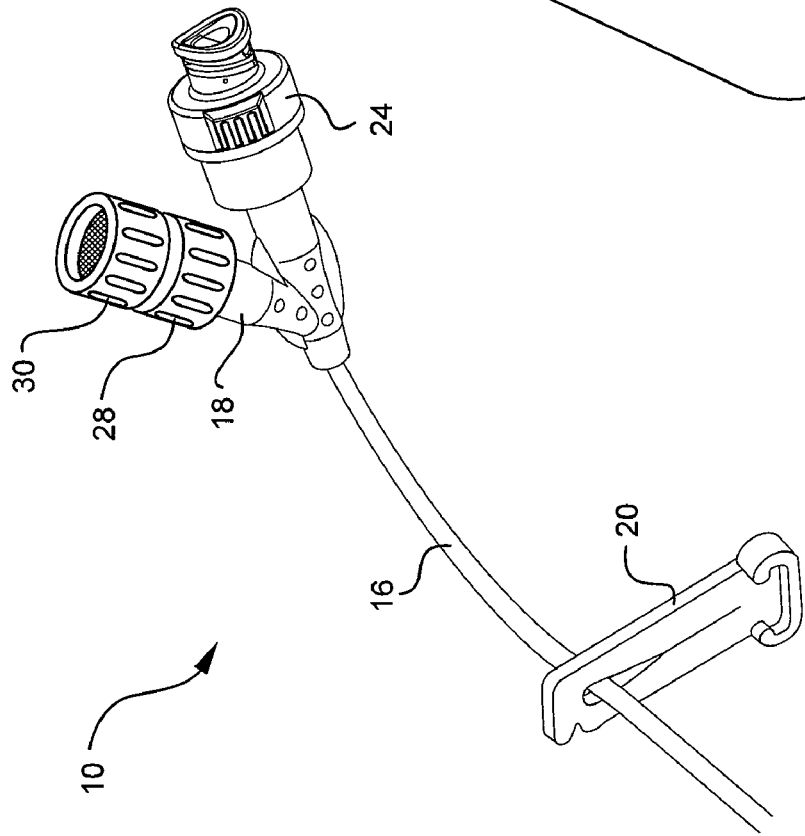

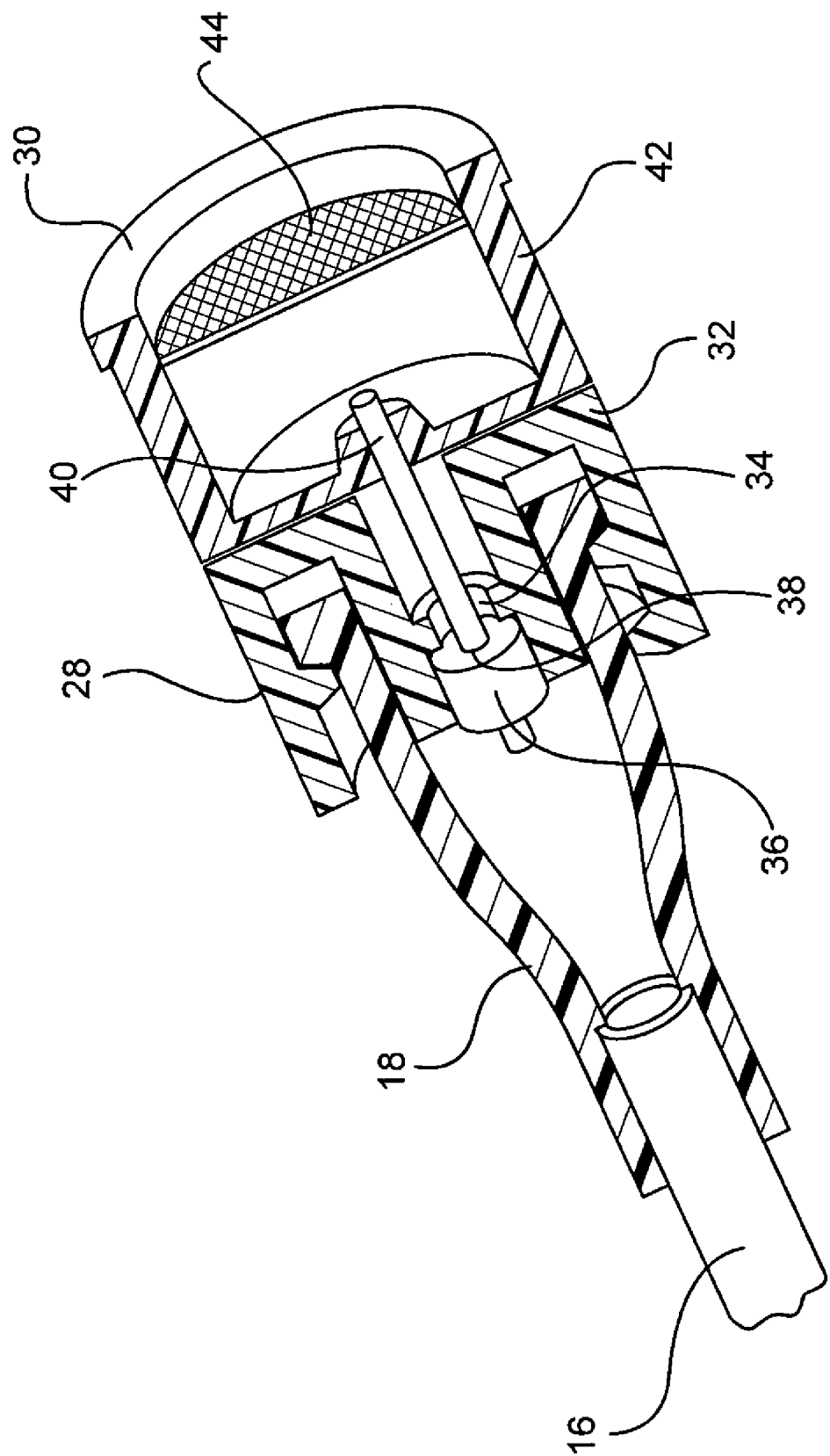

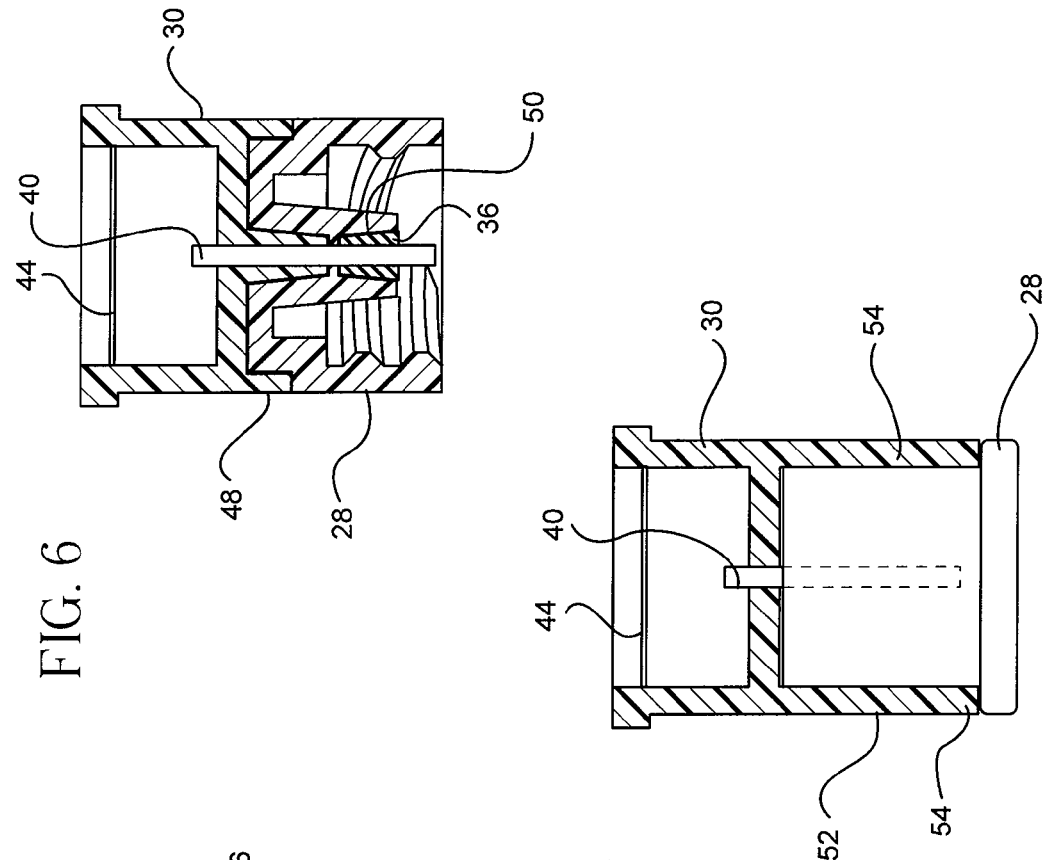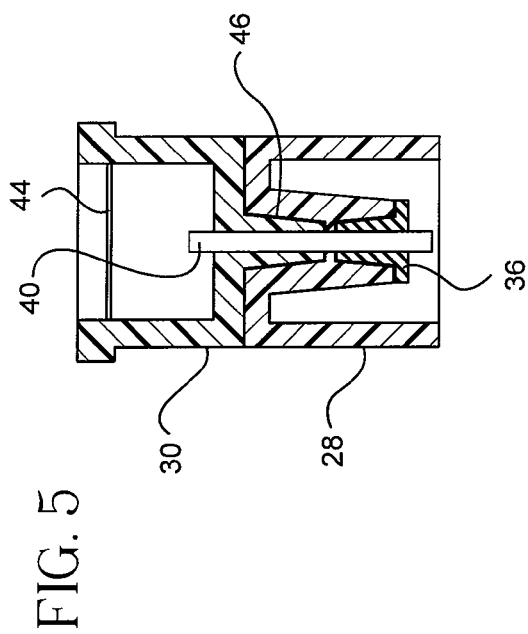

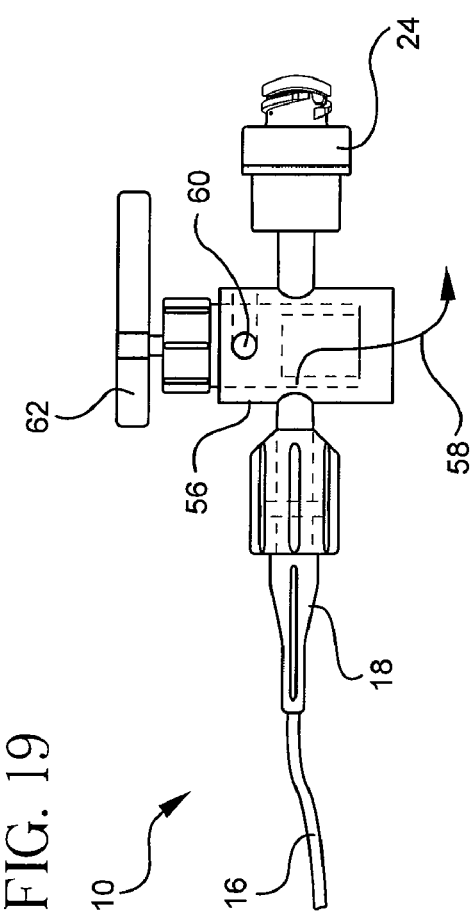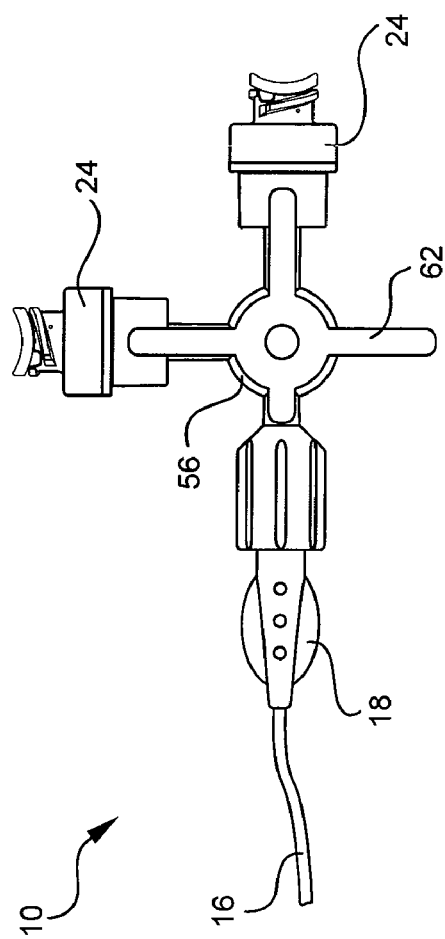

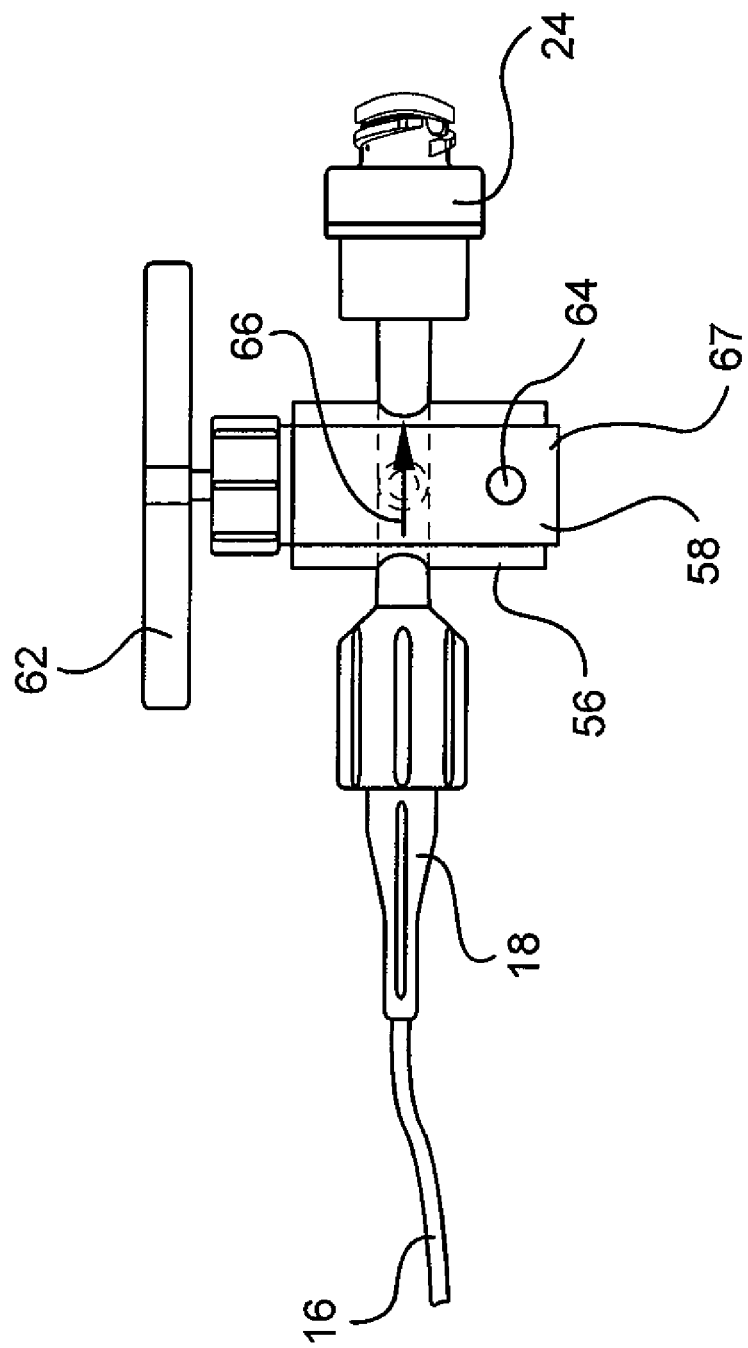

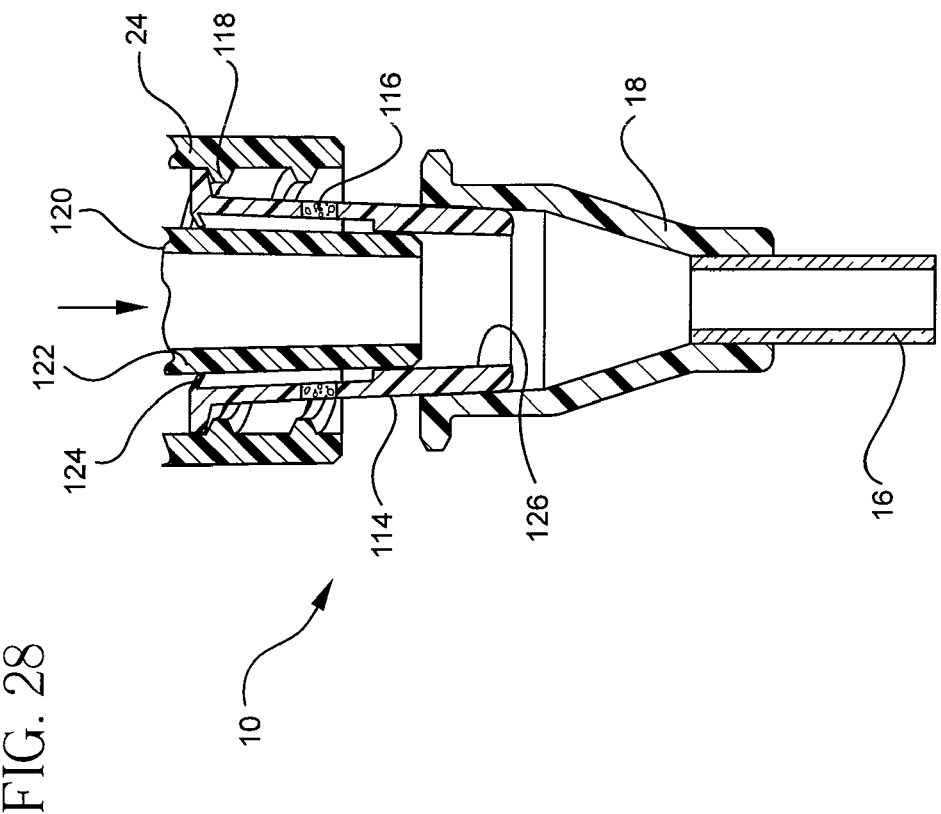
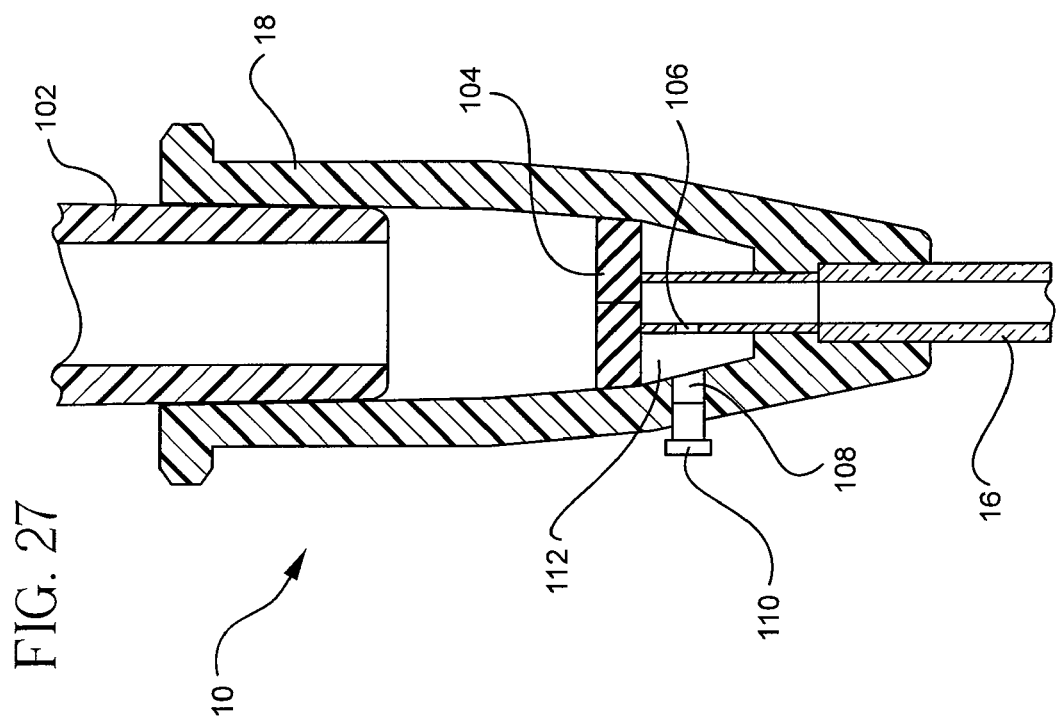

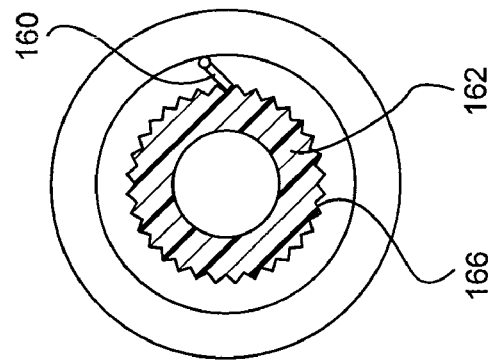
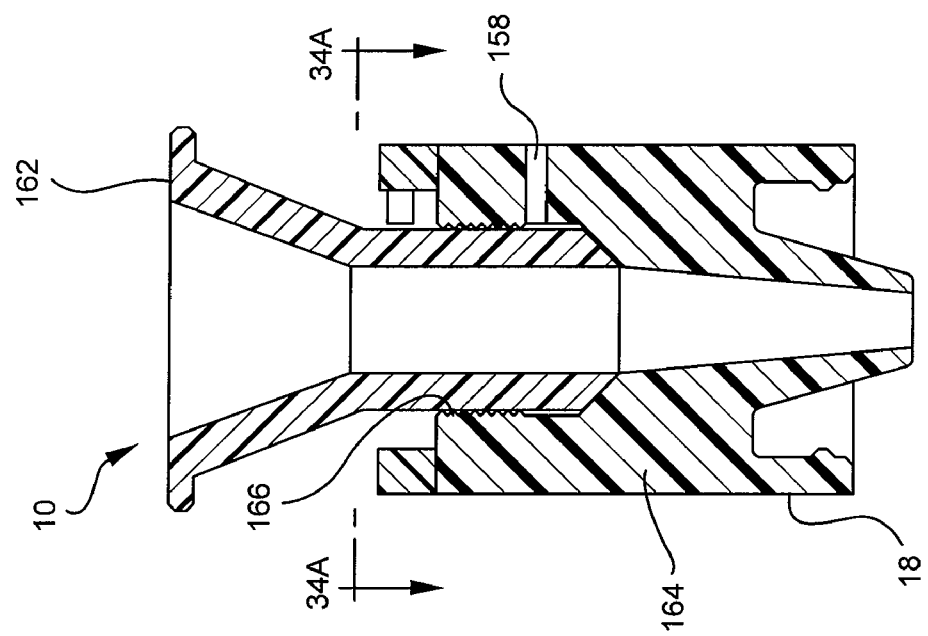
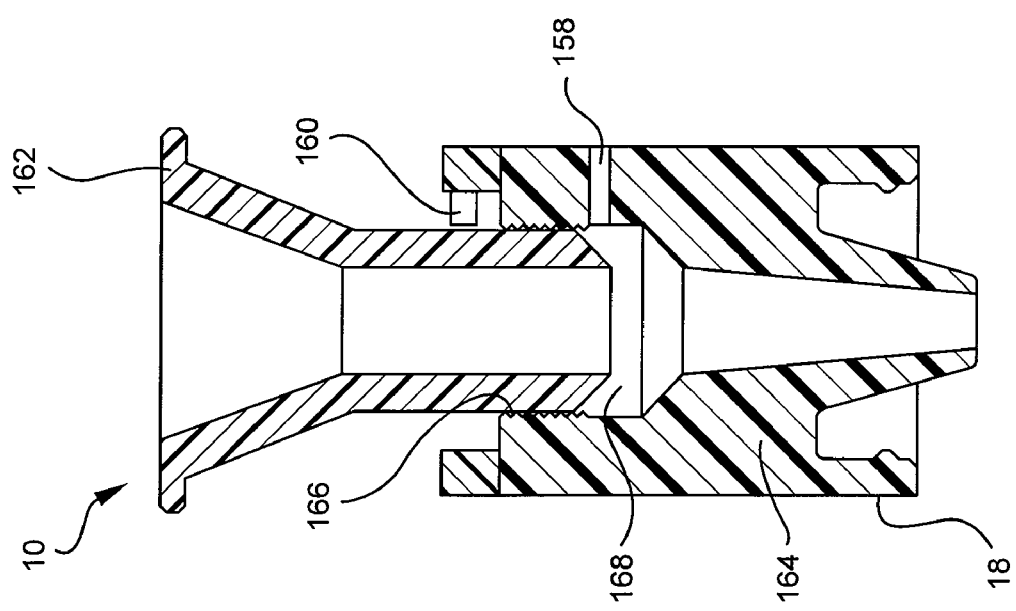

EXTRAVASCULAR SYSTEM VENTING

RELATED APPLICATIONS

This application claims the benefit of U.S. Provisional Application No. 60/864,505, filed Nov. 6, 2006, entitled EXTRAVASCULAR SYSTEM VENTING, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously. A group of vascular access and other devices used to access the vasculature of a patient may be collectively referred to as an extravascular system.

One example of an extravascular system including a catheter is the BD NEXIVA™ Closed IV (intravenous) Catheter System, by Becton, Dickinson and Company. This system includes an over-the-needle, peripheral intravascular catheter made from polyurethane, another catheter used as an integrated extension tubing with a Y adapter and slide clamp, a vent plug, a Luer access port, and a passive needle-shielding mechanism.

The design of the BD NEXIVA™ IV catheter can be described as a closed system since it protects clinicians or operators from blood exposure during the catheter insertion procedure. Since the needle is withdrawn through a septum that seals, after the needle has been removed and both ports of the Y adapter are closed, blood is contained within the NEXIVA™ device during catheter insertion. The pressure exerted on the needle as it passes through the septum wipes blood from the needle, further reducing potential blood exposure. The clamp on the integrated extension tubing is provided to eliminate blood exposure when the vent plug is replaced with another vascular access device such as an infusion set connection or a Luer access port.

A current procedure of initiating the use of an extravascular system such as the BD NEXIVA™ Closed IV Catheter System is as follows. A device operator will insert the needle into the vasculature of a patient and wait for flashback of blood to travel into the device to confirm that the needle is properly located within the vasculature of the patient. The blood travels into and along the catheter of the device because a vent plug permits air to escape the device as blood enters the device. After an operator confirms proper placement, the operator clamps the catheter to halt the progression of blood through the catheter, removes the vent plug, replaces the vent plug with another vascular access device such as an infusion set connection or a Luer access port, unclamps the catheter, flushes the blood from the catheter back into the vasculature of the patient, and re-clamps the catheter.

Many current procedures like the procedure described above present challenges that need to be overcome. For example, the procedure may include an unnecessary number of steps and amount of time to simply insert and prepare an extravascular system for use within the vasculature of a patient. Further, by removing the vent plug, the fluid path of the system is temporarily exposed to potential contamination from the external environment of the extravascular system.

Rather than using a vent plug, some operators attempt to solve the problem above by simply loosening a Luer access device and permitting air to escape from the system during flashback and then tightening the Luer access device to stop blood from advancing along the catheter. Unfortunately, this procedure is also prone to user error, a lack of consistent and accurate control of blood flow through the system potentially leading to blood exposure and loss of body fluids, and unnecessary risk of contamination.

Thus, what are needed are improvements to many of the systems and methods described above. Such systems and methods can be improved by providing more efficient extravascular venting systems and methods.

BRIEF SUMMARY OF THE INVENTION

The present invention has been developed in response to problems and needs in the art that have not yet been fully resolved by currently available extravascular systems, devices, and methods. Thus, these systems, devices, and methods are developed to provide more efficient extravascular venting systems and methods.

A medical device may include a vascular access device forming part of an extravascular system. The vascular access device may be an adapter for at least two other vascular access devices. The adapter may include a gas permeable vent. At least a portion of the vent remains with the adapter after the vent is closed. The at least two other vascular access devices may include at least one catheter.

The vent may include a removable vent plug secured to a ventable end cap. The ventable end cap may seal to close the vent and remain on the adapter after the removable vent plug is removed from the adapter. The vent may also include a gas flow path that is replaced by a fluid flow path when the vent is closed.

The vent may include a pull tab, a ventable material in communication with the pull tab, and a seal in removable communication with the pull tab. The vent may also include a microfiber material. The vent may include a first porous plug and a second porous plug. The first porous plug may be separated from the first porous plug by an air space.

The vent may close upon insertion of a Luer into the adapter. The vent may also or alternatively close upon insertion of a portion of a Luer access device into the adapter. The vent may also or alternatively close upon actuation of a valve in communication with the vent. The vent may also or alternatively close upon actuation of a one-way ratcheting mechanism.

The vent may include a rigid and porous conical plug. The plug may be displaced upon insertion of any portion of any vascular access device into the adapter, such as insertion of the tip of a Luer into the adapter. The vent may include a hydrophobic structure that is displaced when the adapter is accessed by any other vascular access device.

A method of venting a medical device includes providing a vascular access device. The vascular access device may form part of an extravascular system and may function as an adapter for at least two other vascular access devices. The method may also include providing a gas permeable vent as part of the adapter. The method may also include venting gas from the extravascular system through the vent, closing the vent, and maintaining at least a portion of the vent with the adapter after closing the vent.

The vent may include a ventable end cap and a removable vent plug secured to the ventable end cap. The method may then include removing the vent plug from the ventable end cap and sealing the vent with the ventable end cap. Closing the vent may include replacing a gas flow path with a fluid flow path. The vent may also include a pull tab secured to a seal, and the method may include closing the vent by pulling the pull tab.

Venting gas from the extravascular system through the vent may include venting gas through a microfiber. Venting gas from the extravascular system through the vent may also include venting gas through a first porous plug, a second porous plug, and an air space between the first porous plug and the second porous plug.

The method may also include inserting at least a portion of a Luer into the adapter to close the vent. The method may also include inserting at least a portion of a Luer access device into the adapter to close the vent. Closing the vent may include actuating a valve and/or ratcheting a vent closure mechanism. The method may also include displacing at least a portion of the vent with at least a portion of one of the at least two other vascular access devices.

A medical device may include a means for accessing the vascular system of a patient that is connectable to an extravascular system, and a means for venting the extravascular system. The means for venting the extravascular system may form part of the means for accessing the vascular system of a patient.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 2 is a perspective view of an extravascular system having an adapter with a ventable end cap and removable vent plug.

FIG. 3 is a perspective view of the extravascular system of FIG. 2 with the removable vent plug removed.

FIG. 4 is a cross section view of the adapter, ventable end cap, and removable vent plug of FIGS. 2 and 3.

FIG. 5 is a cross section view of a ventable end cap and vent plug with an internal taper connection.

FIG. 6 is a cross section view of a ventable end cap and vent plug with an external connection.

FIG. 7 is a cross section view of a ventable end cap and vent plug with an external length connection.

FIG. 19 is a side view of a vent secured to an adapter.

FIG. 20 is a top view of FIG. 19.

FIG. 21 is a side view of the vent of FIG. 19 in closed position.

FIG. 27 is a cross section view of an adapter with a vent plug and the tip of a male Luer.

FIG. 28 is a cross section view of an adapter and a ventable adapter secured to a closed Luer access device.

FIG. 33 is a cross section view of an adapter with a one-way ratchet.

FIG. 34 is a cross section view of the adapter of FIG. 33 in closed position.

FIG. 34A is a cross section view of the one-way ratchet of FIG. 34.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
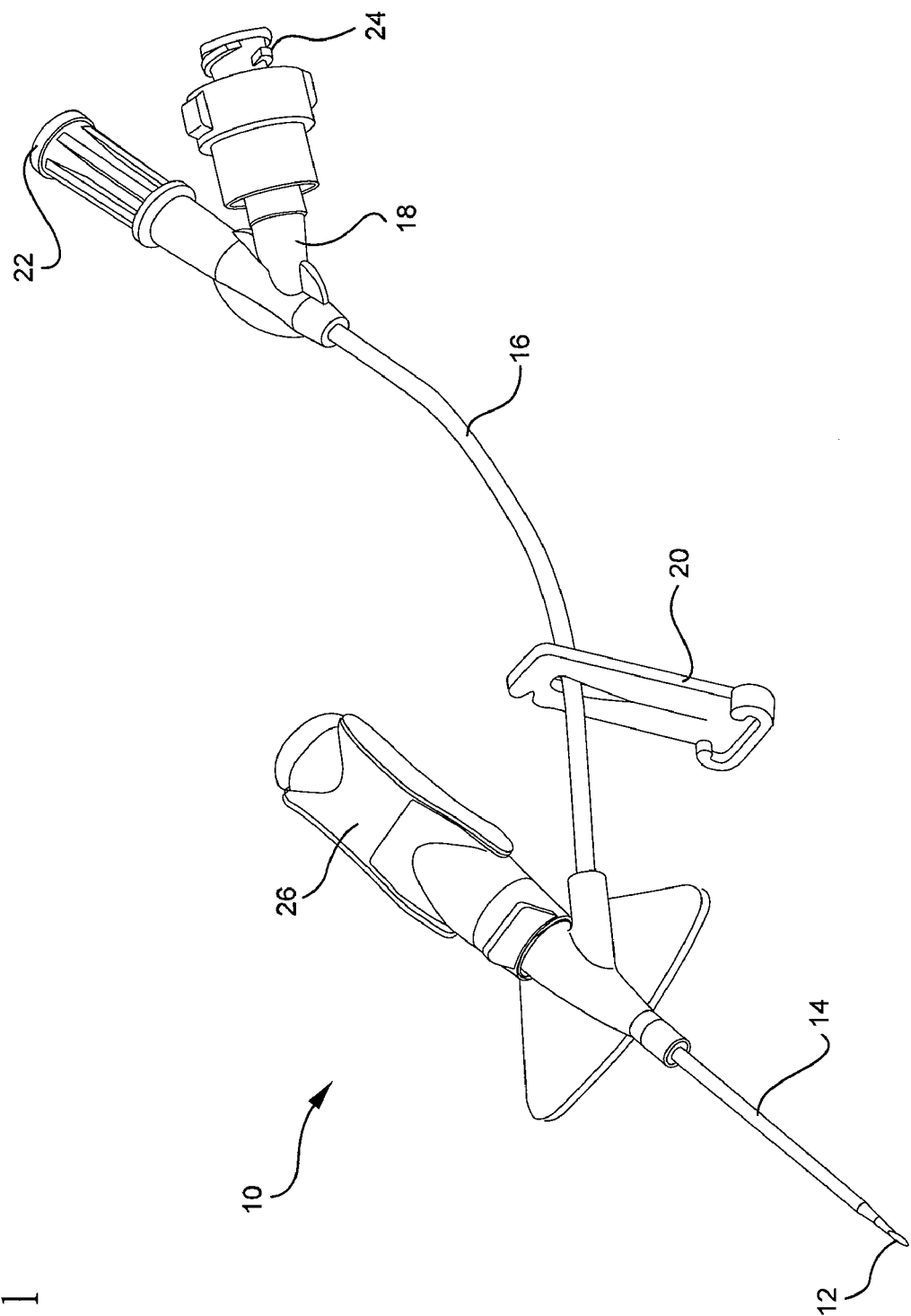
FIG. 1 is a perspective view of an extravascular system.

Referring now to FIG. 1, an extravascular system 10, such as the BD NEXIVA™ Closed IV (intravenous) Catheter System, by Becton, Dickinson and Company, is used to communicate fluid with the vascular system of a patient. An example of the system 10, as shown in FIG. 1, includes an intravascular needle 12; an over-the-needle, peripheral intravascular catheter 14 made from polyurethane; an integrated extension tubing 16 with a Y adapter 18 and slide clamp 20; a vent plug 22; a Luer access port 24; and a passive needle-shielding mechanism 26. Any adapter used to connect two or more vascular access devices may be used in place of the Y adapter 18.

The system 10 is a closed system since it protects clinicians or operators from blood exposure during the catheter 14 insertion procedure. Since the needle 12 is withdrawn through a septum that seals after the needle 12 has been removed and both ports of the Y adapter 18 are closed, blood is contained within the system 10 during catheter 14 insertion. The pressure exerted on the needle 12 as it passes through the septum wipes blood from the needle 12, further reducing potential blood exposure. The slide clamp 20 on the integrated extension tubing 16 is provided to eliminate blood exposure when the vent plug 22 is replaced with another vascular access device such as an infusion set connection or another Luer access port 24.

As mentioned above, a current procedure of initiating the use of the extravascular system 10 is as follows. A device operator will insert the needle 12 into the vasculature of a patient and wait for flashback of blood to travel into the system 10 to confirm that the needle 12 is properly located within the vasculature of the patient. The blood travels into and along the catheter 14 in the space between the needle 12 and the catheter 14. This occurs because a vent plug 22 permits air to escape the system 10 as blood enters the system 10. After an operator confirms proper placement, and after adequate venting of the system 10 has occurred, the operator clamps the extension tubing 16 to halt the progression of blood through the catheter 14, removes the vent plug 22, replaces the vent plug 22 with another vascular access device such as an infusion set connection or a Luer access port similar or identical to Luer access port 24, unclamps the extension tubing 16, flushes the blood from the catheter 14 back into the vasculature of the patient, and re-clamps the extension tubing 16. Alternate vents and venting procedures are desired and will be discussed with reference to the figures following FIG. 1.

Referring now to FIG. 2, an extravascular system 10 includes a ventable end cap 28 and a vent plug 30. The removable vent plug 30 is removably attached to the ventable end cap 28 and permits air venting of the extravascular system 10. The ventable end cap 28 is in turn attached to an adapter 18 which is secured to the extension tubing 16 having a slide clamp 20. A valve or Luer access device 24 may also be attached to the adapter 18.

Referring now to FIG. 3, the extravascular system 10 of FIG. 2 is shown with the vent plug 30 removed from the closed ventable end cap 28. After removal of the vent plug 30, the ventable end cap 28 is sealed. In its closed or sealed position, the ventable end cap 28 permits an operator of the system 10 to use the system after adequate venting and flashback of blood in order to ensure proper placement of the system 10 within the vasculature of a patient.

Referring now to FIG. 4, a cross section perspective view of the removable vent plug 30, ventable end cap 28, adapter 18, and extension tubing 16 is shown. The ventable end cap 28 includes a body 32 having an open channel 34 containing an elastomeric septum 36. The septum 36 has a very small access hole 38 that is sealed under compression in the end cap 28 assembly. The septum hole 38 allows a hollow cannula 40 from the removable vent plug 30 to pass, thereby, providing communication between the atmospheric pressure and the venus pressure of a patient and allowing air to vent and blood to flashback and be visible up the extension tubing 16 or other catheters attached to the extravascular system 10. The vent plug 30 includes a body 42, the attached cannula 40, and an air permeable material 44 or other air filter. The air permeable material 44 allows airflow to pass but prevents fluid from passing. This material 44 may be hydrophobic or hydrophilic and may be a glass, polyethylene terephthalate (PET), a microfiber material, or other synthetic material made of high-density polyethylene fibers, such as TYVEK® material from DuPont.

The system 10 described with reference to FIGS. 2 through 4 allows an integrated catheter system to vent while remaining closed, thereby allowing flashback visualization of blood without exposing a physician to the blood. The system 10 can easily be added to an existing integrated catheter system with a Luer adapter to simplify and reduce the number of steps during administration of a closed system integrated catheter such as the BD Nexiva™ System. Use of this system 10 eliminates the need to open the catheter system between removal of the traditional vent plug 22 (shown in FIG. 1) and subsequent application of an end cap or other vascular access device such as a Luer access device 24. Thus, the ventable end cap 28 and vent plug 30 maintain a closed system 10 at all times, and remove many of the steps described above with reference to FIG. 1 with exception of the step of removing the vent plug 30 and flushing the system 10.

Various alternate embodiments of the ventable end cap 28 and removable vent plug 30 are possible and may be preferred depending upon the use of the system 10. For example, FIG. 5 shows an internal taper connection 46 between the removable vent plug 30 and the ventable end cap 28. FIG. 6 shows an external connection 48 between the removable vent plug 30 and the ventable end cap 28. Various alternate septums, for example, the alternate septum 50 shown in the subset of FIG. 6 may be applied to any of the embodiments described herein.

FIG. 7 illustrates an external full length connection 52 between the removable vent plug 30 and the ventable end cap 28. In the embodiment shown in FIG. 7, the vent plug 30 has walls 54 extended beyond the end of the cannula thereby minimizing any potential for blood exposure to an operator of the system 10 from the tip of the cannula 40, after the removable vent plug 30 has been removed from the system 10.

Figure 9:
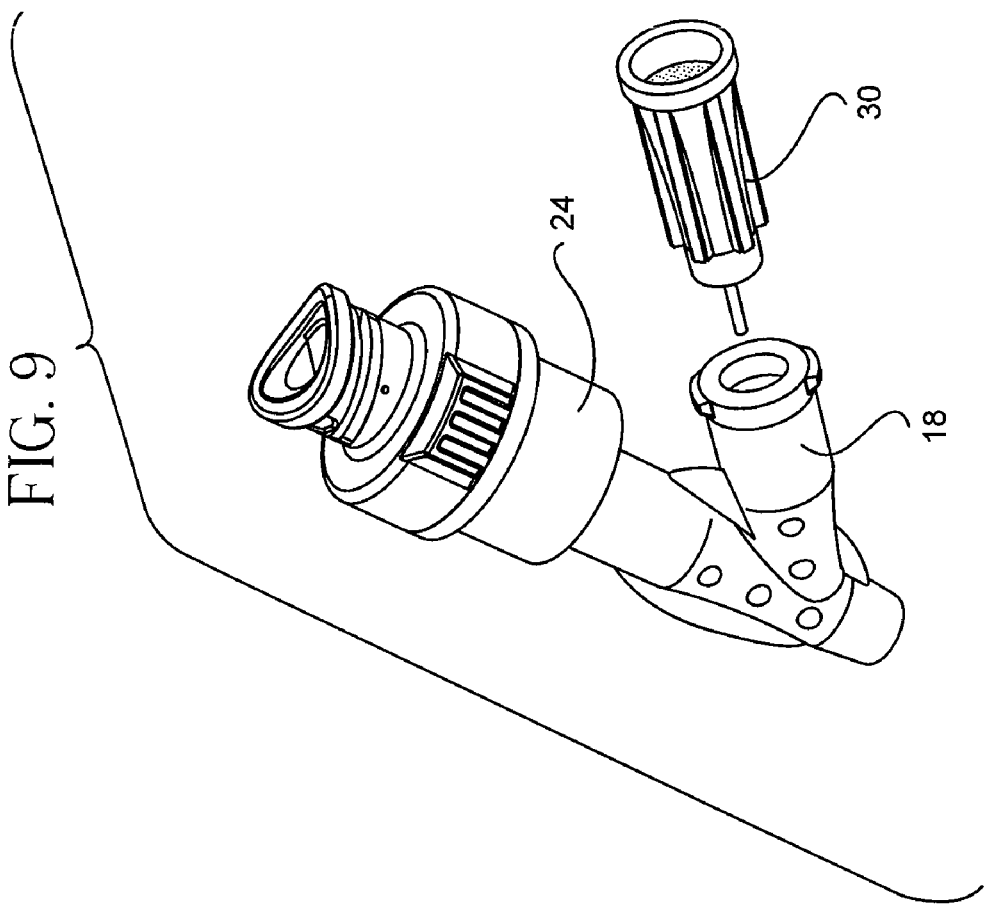
FIG. 9 is a perspective view of the vent plug of FIG. 8 removed from the adapter.
Figure 8:
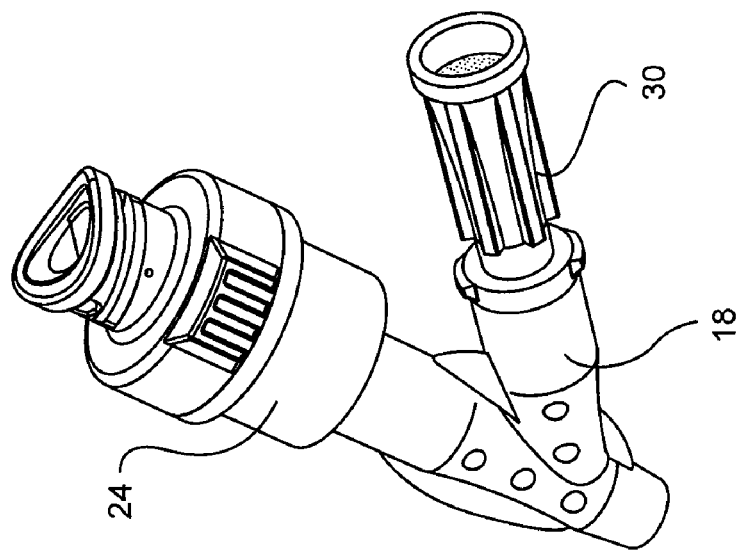
FIG. 8 is a perspective view of an adapter, a closed Luer access device, and a vent plug.

Referring now to FIG. 8, an embodiment of the removable vent plug 30 is secured directly to a Y adapter 18. The Y adapter 18 includes all of the components included within the ventable end cap 28. FIG. 9 illustrates the embodiment of FIG. 8 with the removable vent plug 30 detached from the ventable and sealed Y adapter 18.

Figure 11:
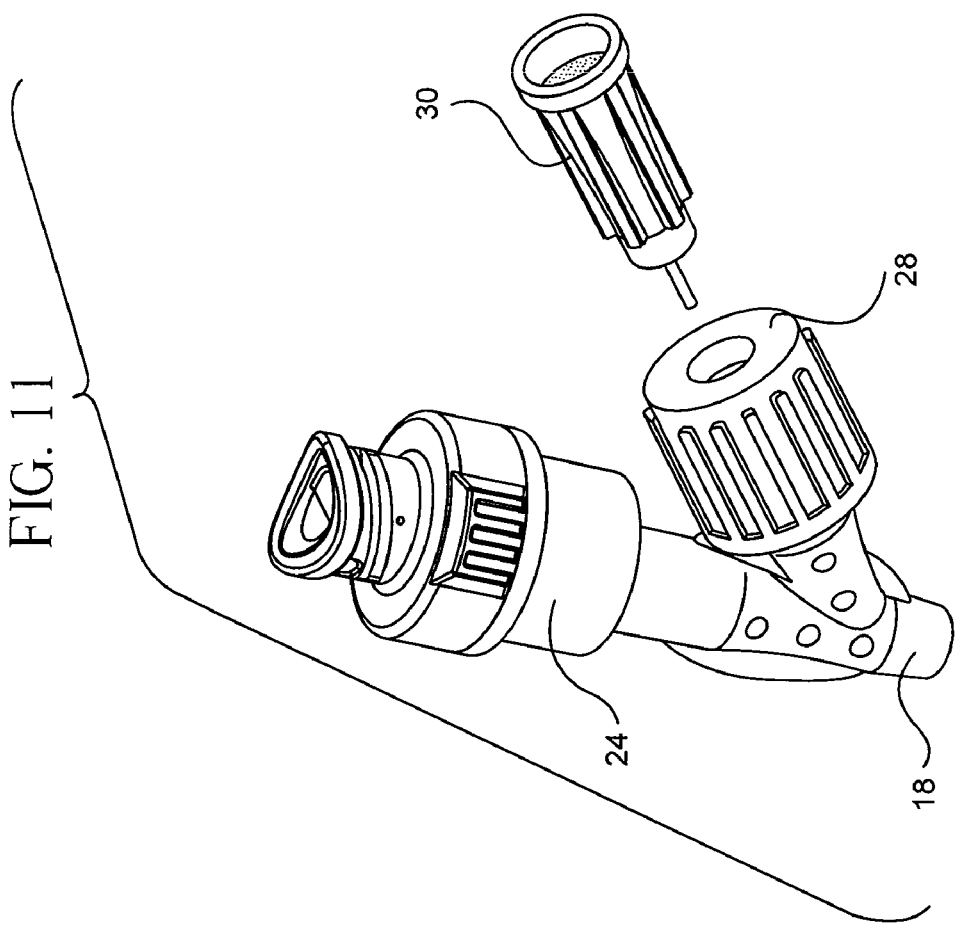
FIG. 11 is a perspective view of the removable vent plug of FIG. 11 removed from the end cap and adapter.
Figure 10:
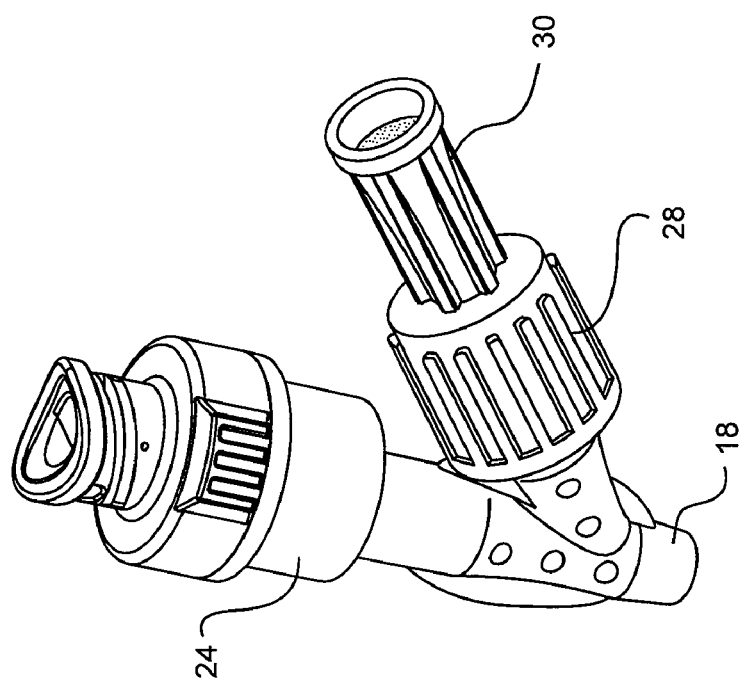
FIG. 10 is a perspective view of a vent plug, an end cap, an adapter, and a closed Luer access device.
Figure 12:
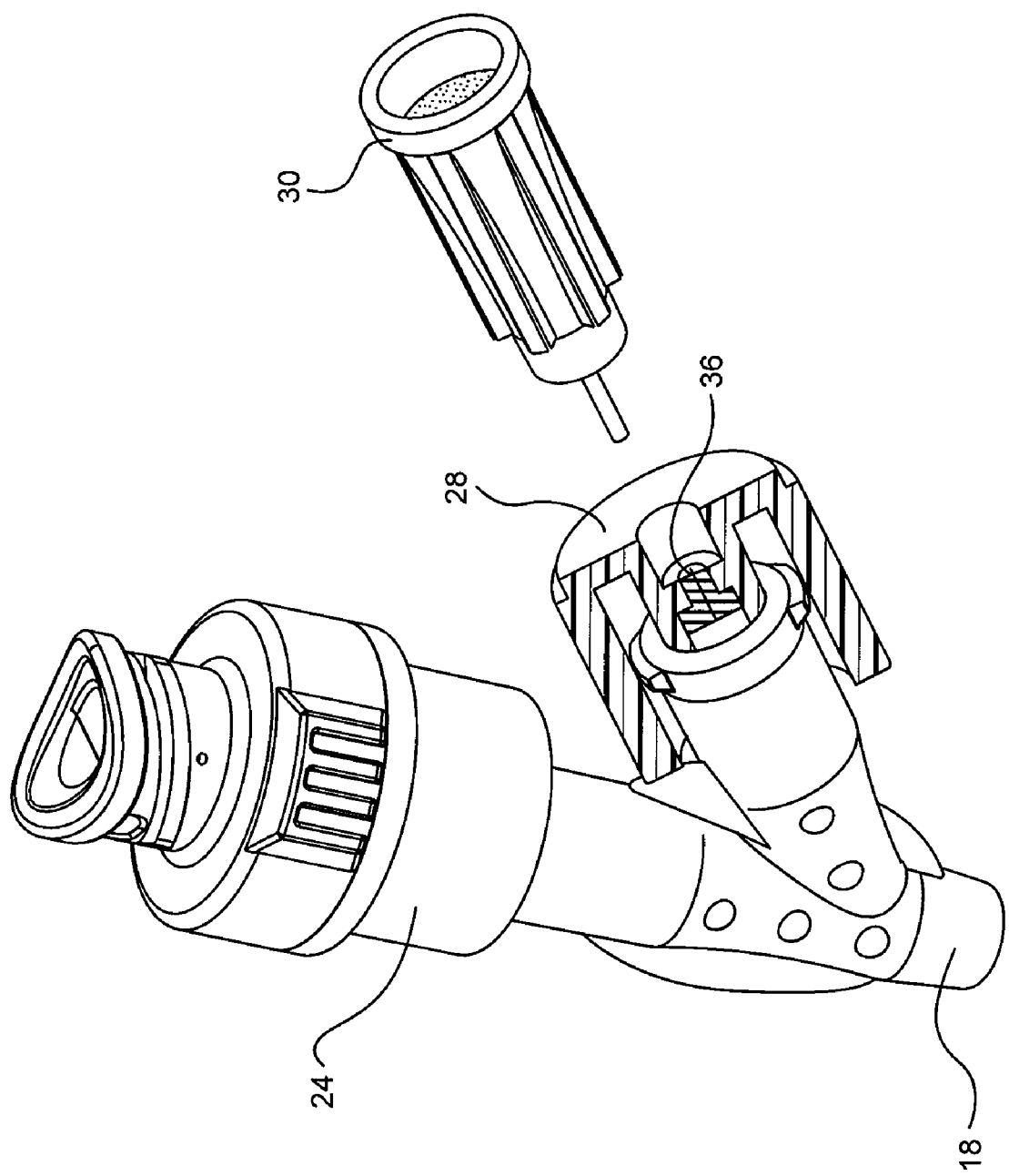
FIG. 12 is a partially cut away perspective view of the removed vent plug of FIG. 11 and a cross section view of the end cap.

FIG. 10 shows an external perspective view of the embodiment described with reference to FIG. 5, with a Y Luer adapter 18 connected to both a Luer access device 24 and a ventable end cap 28 with a removable vent plug 30 secured thereto. FIG. 11 shows a perspective view of the removable vent plug 30 of FIG. 10 removed from the ventable end cap 28 of the system 10. Upon removal, the system 10 remains sealed and closed. FIG. 12 shows a perspective view of the embodiment described with reference to FIGS. 5, 10, and 11, with a cross section view of the ventable end cap 28, revealing the elastomeric septum 36.

Figure 14:
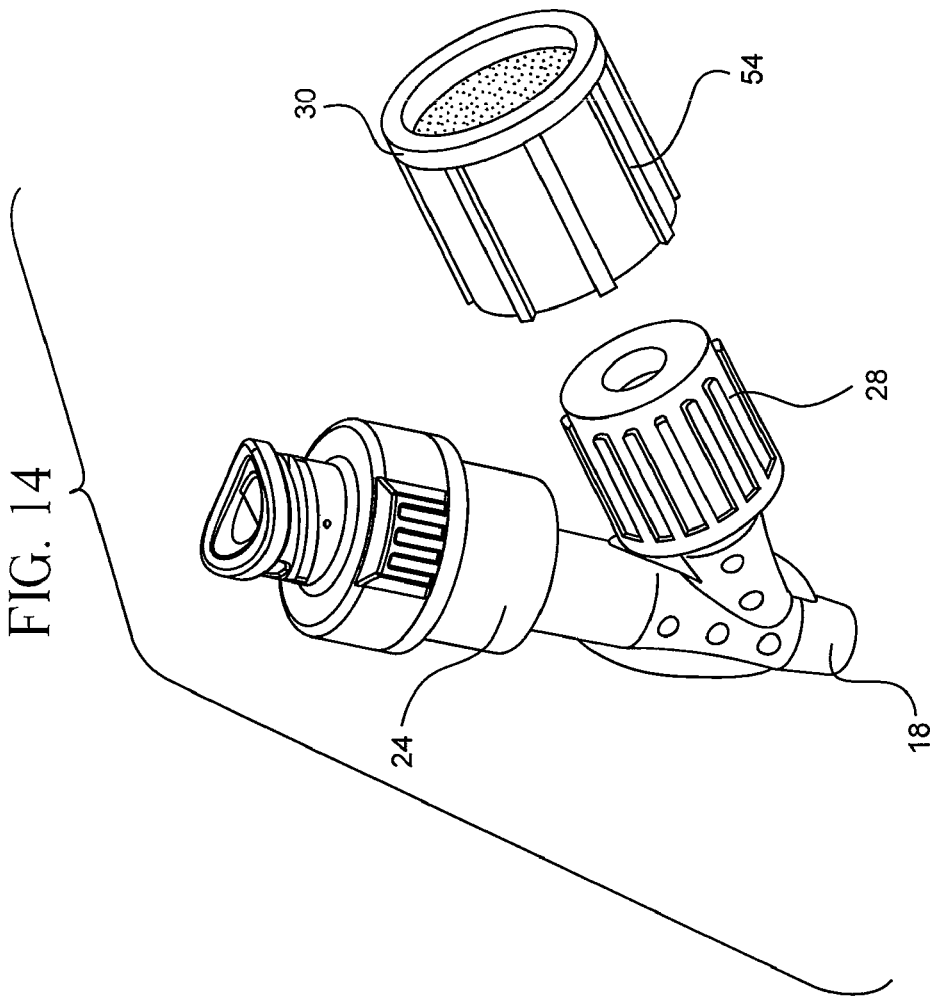
FIG. 14 is a perspective view of the vent plug of FIG. 13 removed from the end cap.
Figure 13:
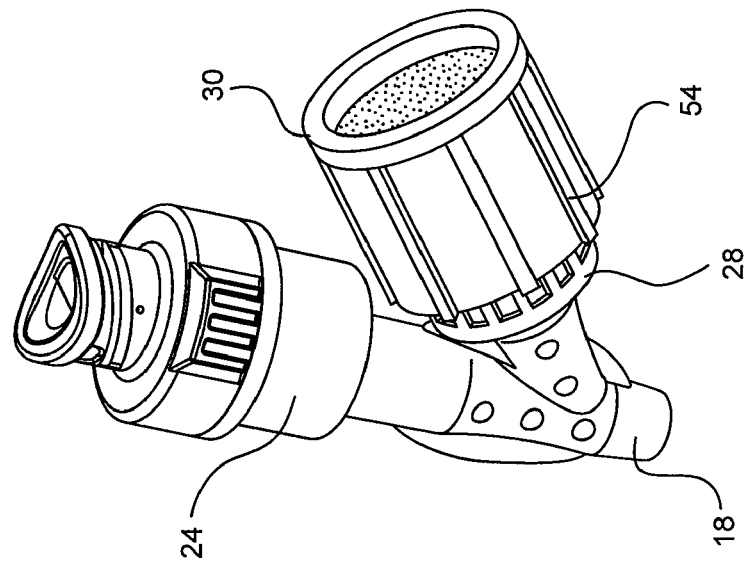
FIG. 13 is a perspective view of the external full length connection between the vent plug and end cap of FIG. 7 as secured to an adapter.
Figure 15:
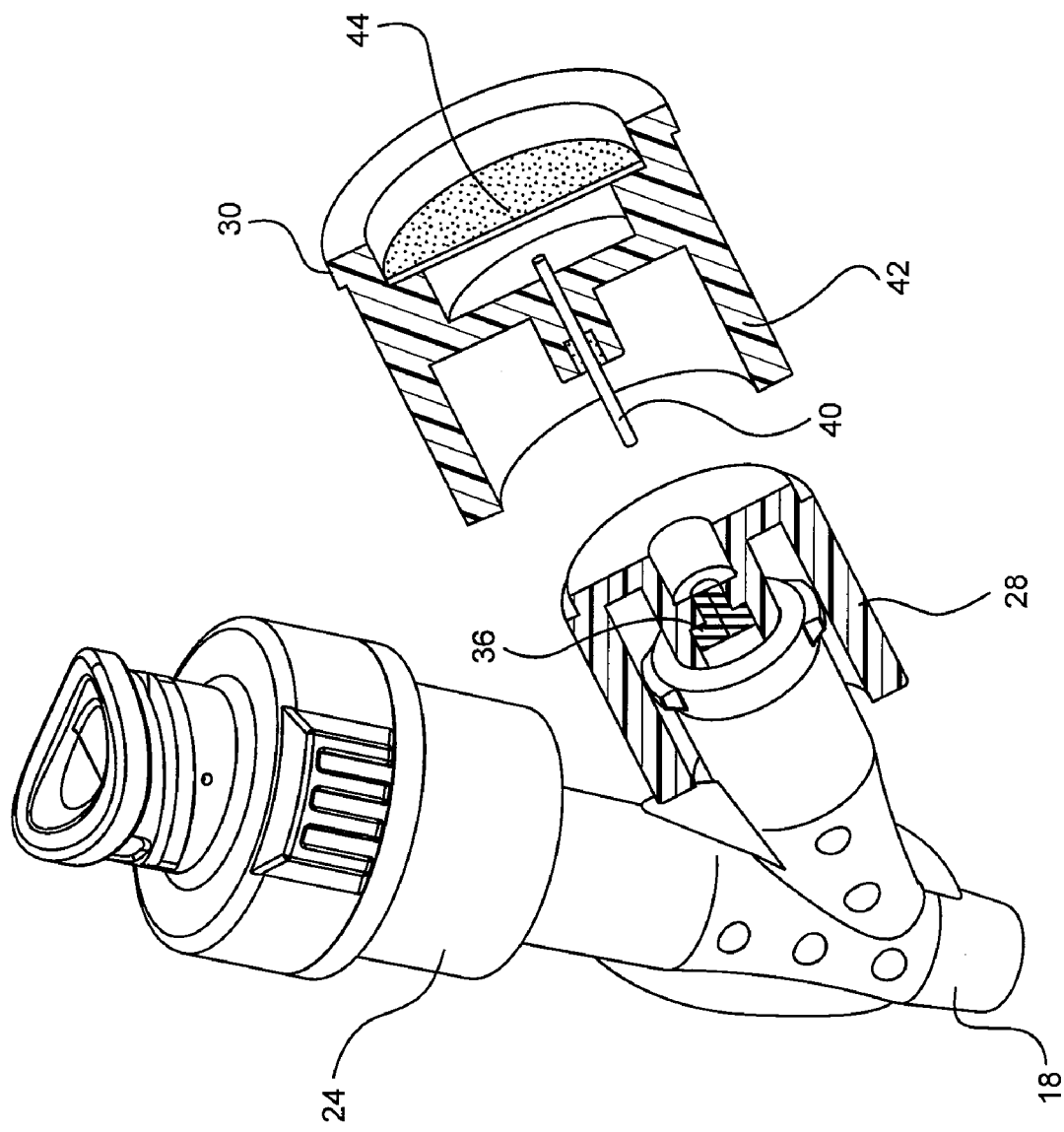
FIG. 15 is a partially cut away perspective view with a cross section view of the vent plug removed from a cross section view of the end cap of FIG. 14.

FIG. 13 is a perspective view of the embodiment described with reference to FIG. 7, illustrating the removable vent plug 30 with extended walls 54 secured to the ventable end cap 28, which is in turn secured to the Y adapter 18 having a Luer access device 24 also attached thereto. FIG. 14 illustrates the embodiment described with reference to FIGS. 7 and 13, with the removable vent plug 30 removed from the ventable end cap 28. FIG. 15 shows the embodiment described with reference to FIGS. 7, 13, and 14 in perspective view, with a cross section view of the removable vent plug 30 and the ventable end cap 28. The removable vent plug 30 shows the breathable or air permeable media 44 and the cannula 40 attached to the body 42 of the removable vent plug 30. The ventable end cap 28 includes the elastomeric septum 36.

Any embodiment including a removable vent plug 30 may, and preferably will, include a cannula 40 that is blunt. A blunt cannula, will minimize the risk of injury to an operator of the system 10.

Figure 17:
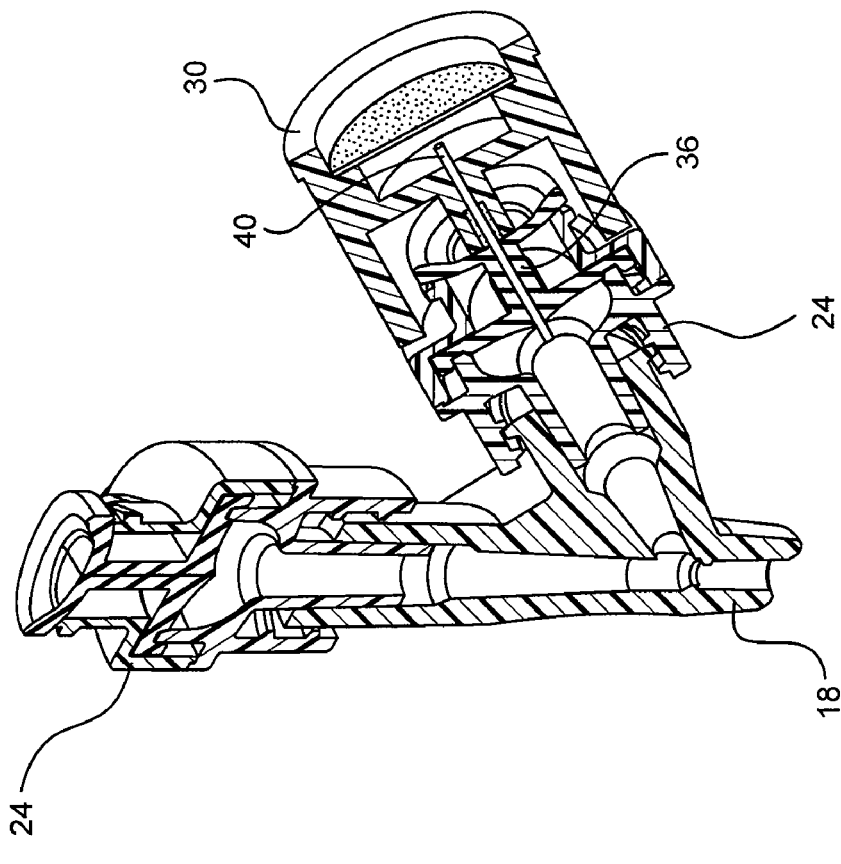
FIG. 17 is a cross section view of FIG. 16.
Figure 16:
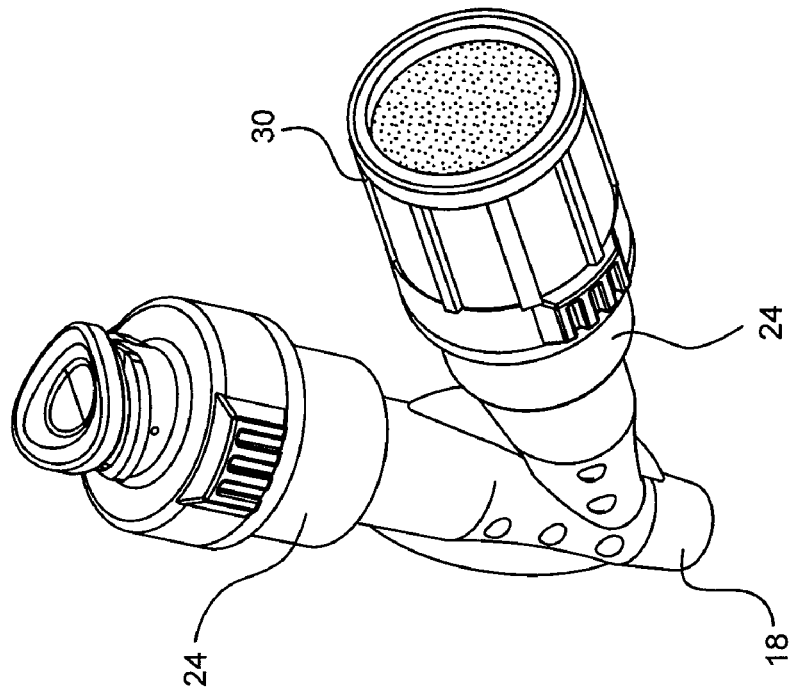
FIG. 16 is a perspective view of a vent plug secured to a closed Luer access device on an adapter.
Figure 18:
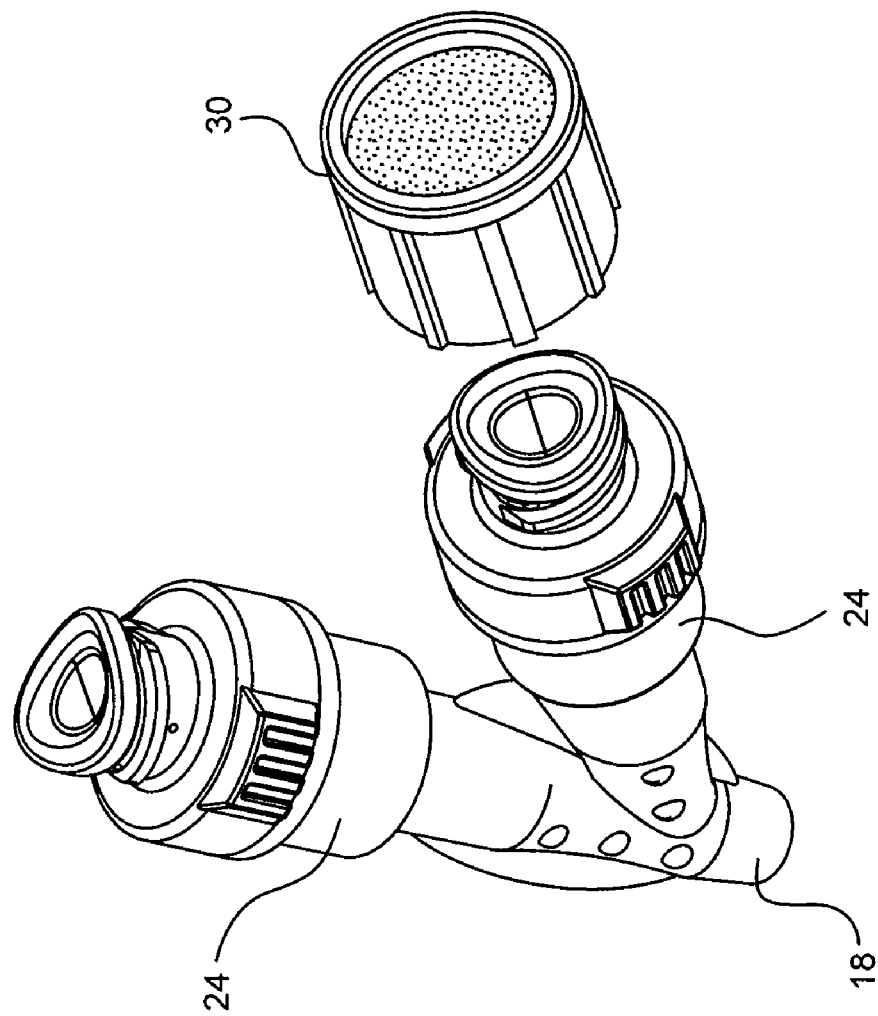
FIG. 18 is a perspective view of the vent plug of FIG. 16 removed from the closed Luer access device.

Referring now to FIG. 16, rather than attaching to a ventable end cap 28 or directly to the Y adapter 18, the removable vent plug 30 may be attached to any other vascular access device, such as a closed Luer access device 24. FIG. 17, which is a cross section view of the embodiment described with reference to FIG. 16, illustrates that the closed Luer access device 24 includes an elastomeric septum 36 capable of sealing after the blunt cannula 40 of the removable vent plug 30 is removed from the device 24. FIG. 18 shows a perspective view of the embodiment described with reference to FIGS. 16 and 17, having the removable vent plug 30 detached from the Luer access device 24.

Thus, the embodiments described with reference to FIGS. 2 through 18 are directed to a vascular access device with a gas permeable vent including a removable vent plug 30 that may be removed from a ventable end cap 28, permitting the ventable end cap 28 to seal and close the vent and remain on the adapter 18 after the removable vent plug is removed from the adapter 18. Another embodiment, described with reference to the following figures, describes a vent which includes a gas flow path that is replaced by a fluid flow path when the vent is closed.

Referring now to FIG. 19, an extravascular system 10 includes a vent 56 secured to an adapter 18 which is in turn secured to the extension tubing 16 of the system 10. At least one other vascular access device such as a closed Luer access device 24 is secured to the vent 56. The vent 56 includes a gas flow path 58 that is replaced by a fluid flow path 66 (FIG. 21) when the vent hole 64 (FIG. 21) is closed and a fluid hole 60 is opened. An operator may close the vent 56 by actuating, pushing, rotating, or otherwise activating or seating, a lever 62, or similar mechanism attached to the vent 56.

Referring now to FIG. 20, a top view of the vent 56 of the embodiment described with reference to FIG. 20 is shown. The lever 62 is shown in open position, such that the gas flow path 58 transfers gas from the extension tubing 16 through the adapter 18 and into the vent 56 to the surrounding atmosphere. After the lever 62 is rotated, or otherwise pushed or activated, the gas flow path 58 will be replaced with a fluid flow path 66 (FIG. 21), communicating fluid from the adapter 18 into the one or more Luer access devices 24.

Referring now to FIG. 21, the vent 56 described with reference to FIGS. 19 and 20 is shown having the lever 62 activated, seated, or otherwise actuated to close the gas flow path 58 by sealing the vent hole 64 of the vent 56 and to open the fluid flow path 66 from the adapter 18 through the vent 56 and into the at least one Luer access device 24. The vented portion 67 of the vent 56 described with reference to FIGS. 19 through 21 may have its outer opening sealed with a breathable or other air permeable material that allows air flow but prevents fluids from crossing the material. This material may be any vent material described in this disclosure or any equivalent thereof.

The embodiment described with reference to FIGS. 19 through 21 thus provides a vascular access device with a gas permeable vent 56 which includes a gas flow path 58 that is replaced by a fluid flow path 66 when the vent 56 is closed. The vent 56 maintains a closed system 10 at all times and removes all of the conventional venting steps with exception of flushing the system 10 and adds the additional step of actuating the lever 62 of the vent 56.

Figure 22:
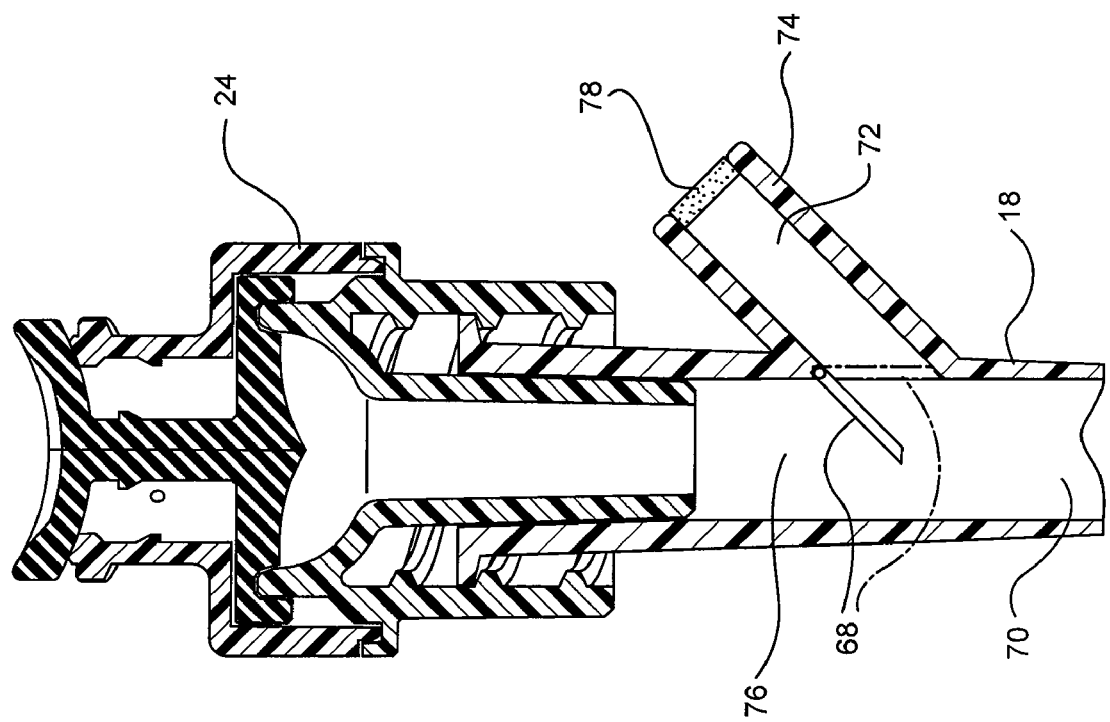
FIG. 22 is a cross section view of an adapter with a valve.

Referring now to FIG. 22, an embodiment alternate to that described with reference to FIGS. 19 through 21 also provides a gas flow path that is replaced by a fluid flow path when a vent is closed. As shown in FIG. 22, an extravascular system 10 includes a vascular access device such as a closed Luer access device 24 secured to an adapter 18. The adapter 18 includes a valve 68 located within the adapter 18 at the junction of multiple fluid paths. The valve 68 is set to open position by means of a spring or other mechanism capable of setting the valve 68 in a position where the downstream path 70 of the adapter 18 is in communication with an upstream gas flow path 72 in the air vent portion 74 of the adapter 18.

In its open position, the valve 68 closes the fluid flow path 76 of the portion of the adapter 18 leading to the device 24. With the valve 68 open, an operator may vent the system 10 by allowing air to escape from the path 70 through the gas flow path 72 and out an air filter 78. The air filter 78 may include any venting material included in this disclosure and may also include any porous plastic material such as Porex. After venting, an operator may infuse fluids through the device 24 into the fluid flow path 76, causing the fluid infusion pressure to close the valve 68 and travel downstream into the flow path 70. As the valve 68 closes, it will latch against the opposite surface of the adapter 18 in the air vent portion 74, causing the valve 68 to remain in closed position throughout the continued use of the system 10.

Figure 23:
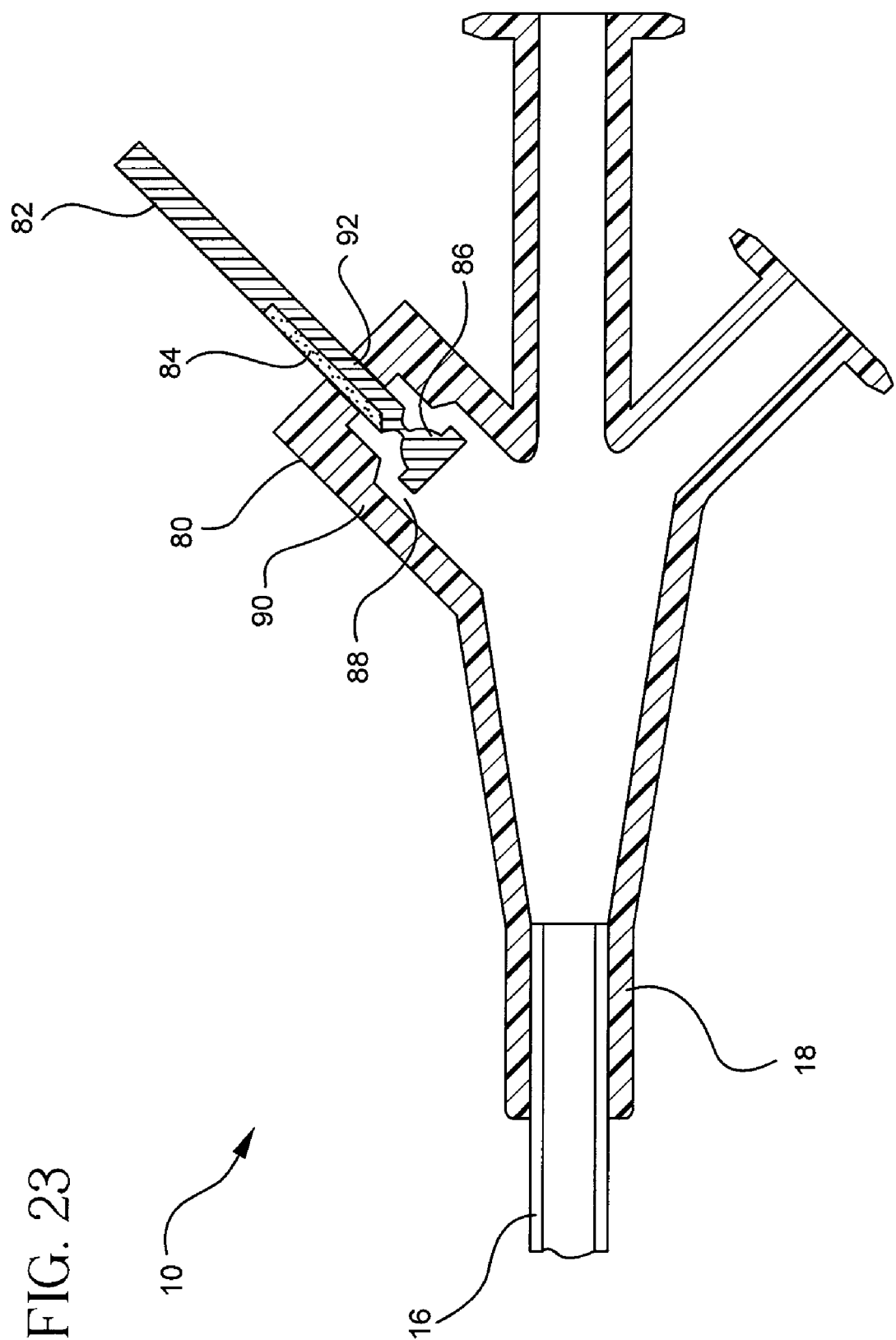
FIG. 23 is a cross section view of an adapter with a pull tab and seal.

Referring now to FIG. 23, an extravascular system 10 includes an adapter 18 secured to extension tubing 16. The adapter 18 may include a ventable portion 80. The ventable portion 80 includes a pull tab 82 including a ventable material 84 on at least a portion of the pull tab 82, and a seal 86 in removable communication with the pull tab 82. In operation, an operator may permit air or other gas to escape the system 10 through the ventable portion 80, since there are air gaps 88 between the body 90 of the adapter 18 and the seal 86. The air will travel through the ventable material 84 and escape to the surrounding environment of the system 10. An operator may terminate the venting of the adapter 18 by pulling the pull tab 82 until the seal 86 is securely lodged within a narrow neck 92 of the ventable portion 80 and the pull tab is removed, or breaks free from, the seal 86.

Figure 24:
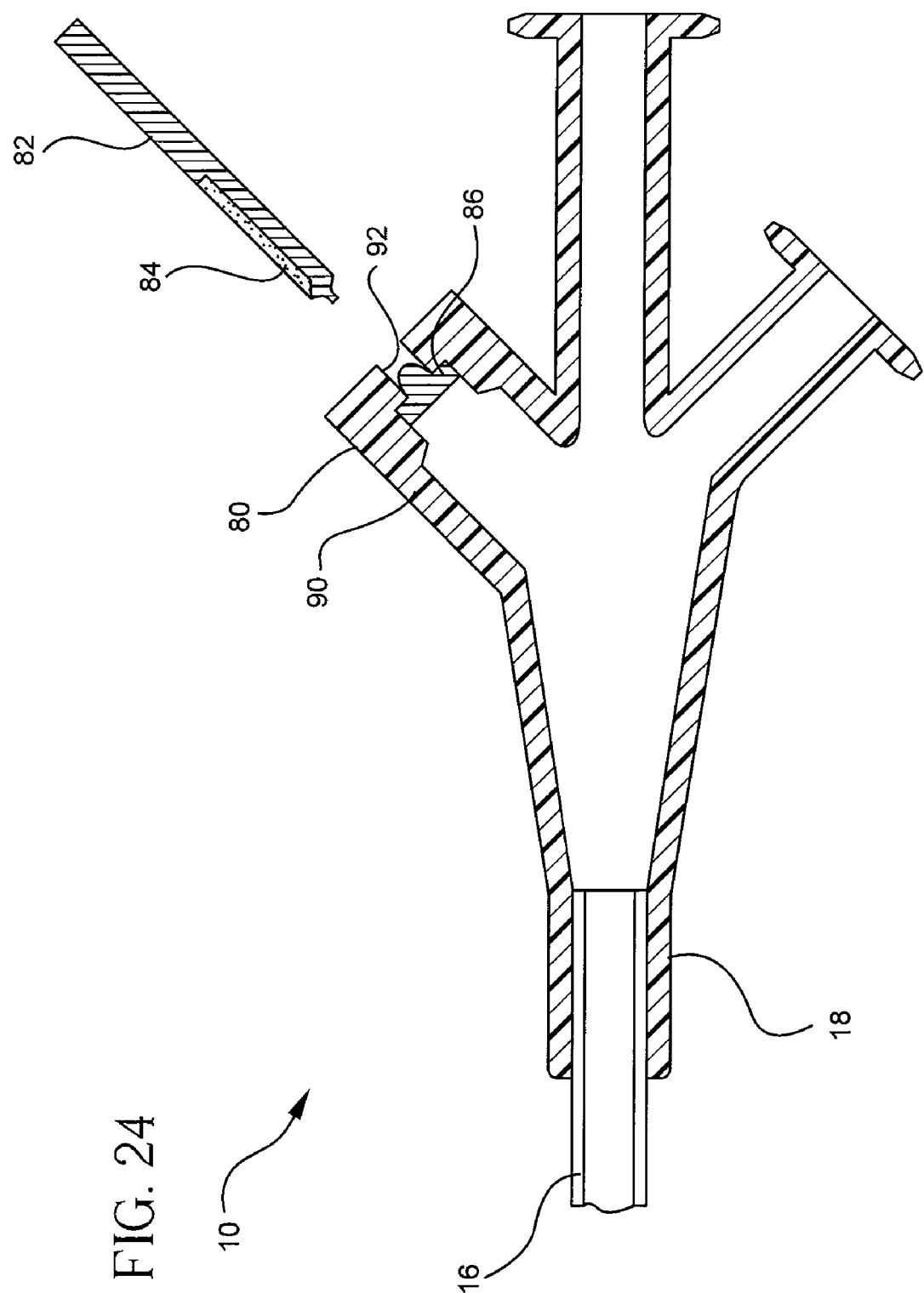
FIG. 24 is a partial cross section view of the pull tab of FIG. 23 removed from the seal.

Referring now to FIG. 24, a partial cross section view of the ventable portion 80 of the adapter 18 is shown. The pull tab 82, with its ventable material 84 has been removed from the seal 86, which seal 86 is now a permanent plug for the adapter 18, inhibiting any air or fluid from further escaping the adapter 18. The breathable, air permeable, ventable material 84 may be any vent material described in this disclosure.

Figure 25:
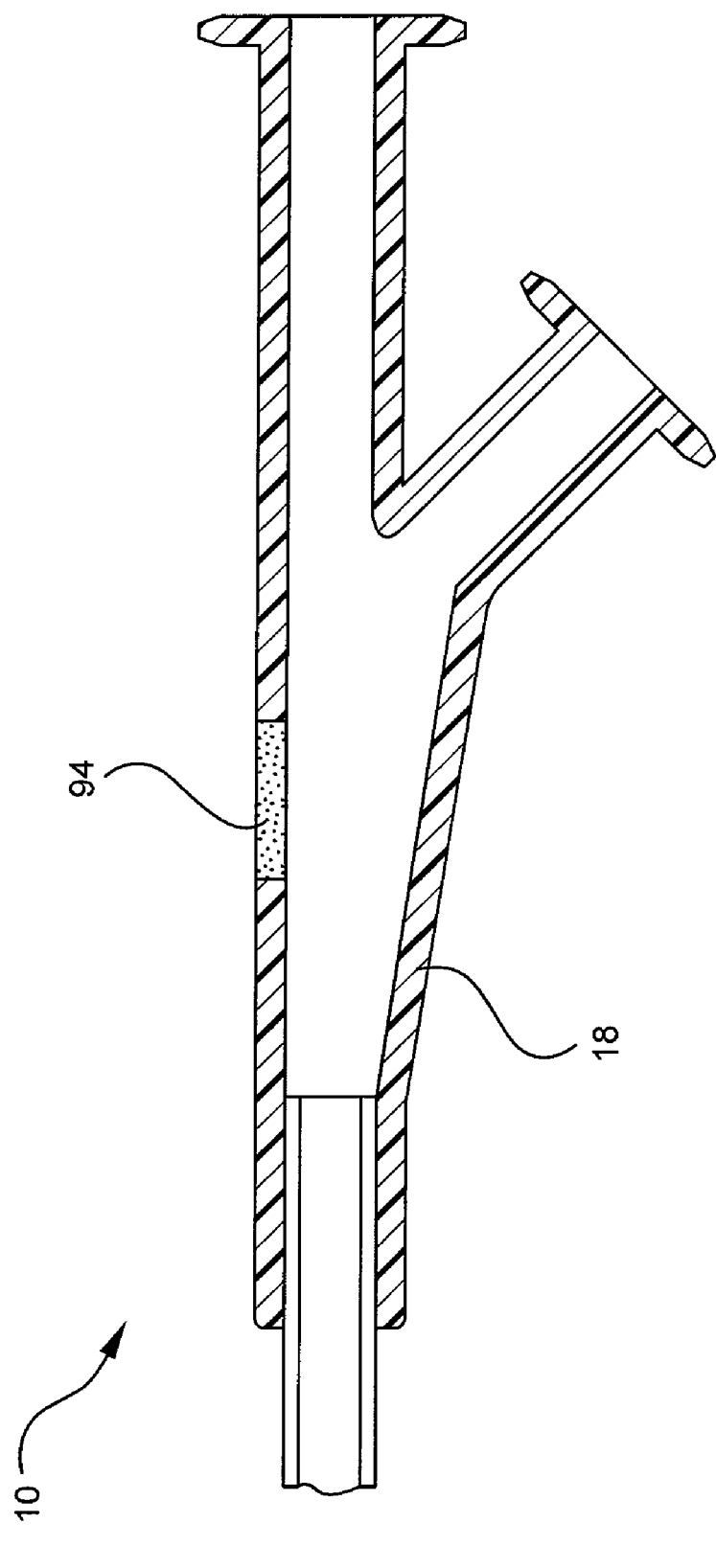
FIG. 25 is a side view of an adapter with a microfiber material.

Referring now to FIG. 25, a microfiber window 94, made of any venting material described in this disclosure, including GOR-TEX® fabric, on the side of any inside surface of the adapter 18. The venting window 94 may be included on any vascular access device described in this disclosure. The venting window 94 may be used in combination with any other element or embodiment described within this disclosure. The microfiber window 94 permits air or other gas to vent through the window, but prevents any fluid from escaping therethrough. After all gas has been vented from the system 10, the adapter 18, and microfiber window 94, may be flushed clean by an operator with a cleaning fluid such as saline.

Figure 26:
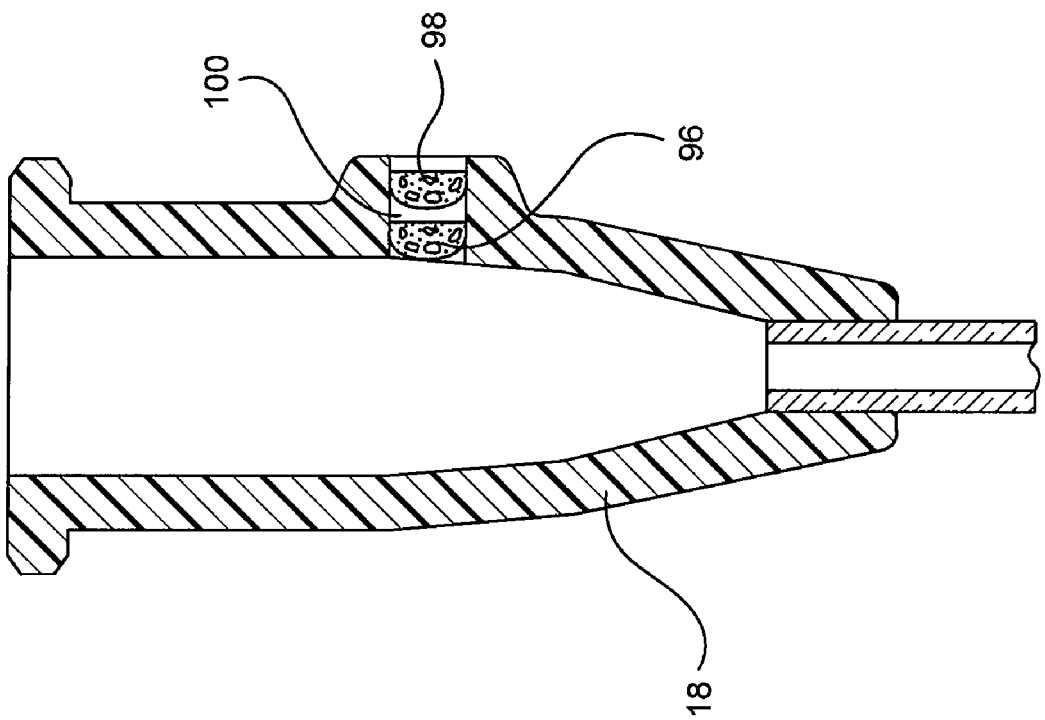
FIG. 26 is a cross section view of an adapter with a vent.

Referring now to FIG. 26, an extravascular system 10 includes an adapter 18 having a first porous plug 96 separated from a second porous plug 98 by means of an air space 100. The first and second porous plugs 96 and 98 are formed on any surface of the body of the adapter 18 through which air or other gas is desired to be vented from the system 10 to the external atmosphere. The first porous plug 96 is located on the interior surface of the adapter 18 and functions as a primary liquid and pressure stop for the adapter 18. The air space 100 allows weeping of fluid under pressure from the first porous plug 96 into the air space 100. The second porous plug 98 is on the external surface of the adapter 18 and provides a second pressure or fluid stop capable of preventing the fluid that has wept from the first porous plug 96 into the air space 100 to escaping the adapter 18. Thus, the first and second porous plugs 96 and 98 in combination with the air space 100 provide a vent that is capable of venting all air or gas from the adapter 18 without permitting any fluid escape.

Referring now to FIG. 27, an extravascular system 10 includes an adapter 18 with a vent that closes upon insertion of a portion of a Luer 102 into the adapter 18. The adapter 18 includes a split septum 104 separating the internal components of the adapter 18 from the external environment. The split septum 104 will separate upon Luer 102 insertion into the adapter 18 by force of the tip of the Luer 102. The split septum 104 protects a hole 106 within an extension tube 16 which vents air or other gas through a vent hole 108, and a vent plug 110 located within the vent hole 108, to escape from the Luer adapter 18 into the external atmosphere. The vent plug 110 is located within the hole 108 through the body of the adapter 18. After the Luer 102 is inserted into the adapter 18, the split septum 104 separates and moves downward into the lower chamber 112 of the adapter 18, sealing the hole 108 of the Luer adapter 18 and the hole 106 of the extension tube 16.

Referring now to FIG. 28, an extravascular system 10 includes an adapter 18 through which a vascular access device and ventable adapter 114 may attach. The ventable adapter 114 is secured to the male Luer of a Luer access device 24, capable of venting the system 10 upon initial insertion into the adapter 18, prior to being torqued, or otherwise fully attached to the adapter 18. The ventable adapter 114 includes venting holes 116 with a semi-permeable material, such as any vent material included in this disclosure.

After venting has adequately occurred in the system 10, a user will torque the Luer access device 24, causing its threads 118 to direct the Luer access device 24 in a downward direction 120 towards the remainder of the ventable adapter 114. As an internal male Luer 122 of the device 24 proceeds in a direction 120, the Luer 122 will crush the upper seals 124 in the ventable adapter 114 and the lower surface of the Luer 122 will come into sealing contact with the internal contact area 126 of the ventable adapter 114. When the lower portion of the Luer 122 is sealed against the internal contact area 126 of the ventable adapter 114, the ventable adapter 114 is fully sealed, causing the venting holes 116 from permitting any additional air or gas from escaping through the ventable adapter 114. Thus, the embodiment described with reference to FIG. 28 describes a vent that closes upon insertion of a portion of a Luer access device 24 into an adapter 18.

Figure 29:
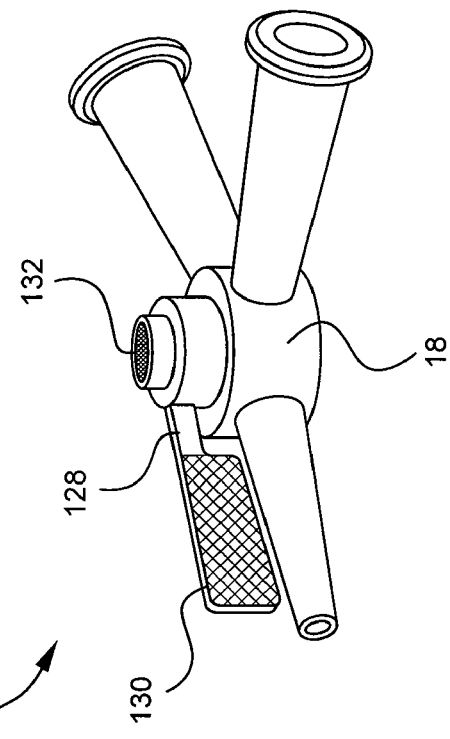
FIG. 29 is a perspective view of an adapter with an on/off valve.

Referring now to FIG. 29, an extravascular system 10 may include a Y adapter 18 with a vented on/off valve 128 capable of closing the vent of the adapter 18 upon actuation of the valve 128. As shown in FIG. 29, the on/off valve 128 is in on, or open, position 130, permitting air to escape the extravascular system 10 through a removable vent plug 132. The vent described with reference to FIG. 29, and the following FIG. 30, may be used with a 3-way stop cock.

Figure 30:
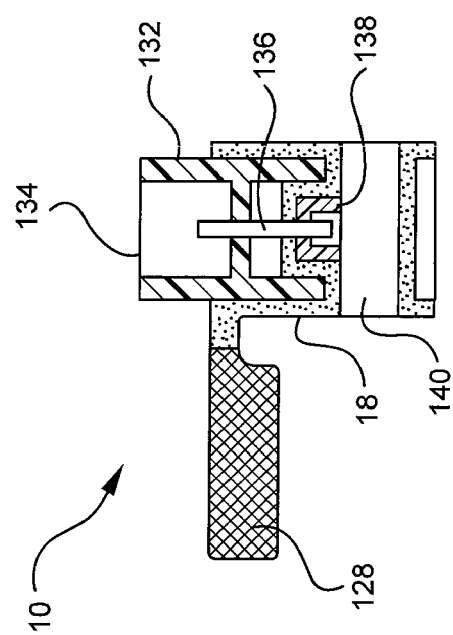
FIG. 30 is a cross section view of the on/off valve of FIG. 29.

Referring now to FIG. 30, the embodiment described with reference to FIG. 29 is shown in cross section view, revealing the internal components of the adapter 18. The adapter 18 includes the on/off valve 128 in communication with the vent plug 132. The vent plug 132 includes a breathable hydrophobic membrane 134 or any other vent material described in this disclosure and any equivalent thereof. The vent plug 132 is connected by means of a cannula 136 to a septum 138 of the remaining portion of the adapter 18. An air channel 140 beneath the septum 138 communicates through the cannula 136 into the vent plug 132 allowing air or other gas to escape through the membrane 134 when the on/off valve 128 is in the on position 130, as shown in FIG. 29. Thus, the embodiment described with reference to FIGS. 29 and 30 illustrates a vascular access device with a gas permeable vent capable of venting gas from an extravascular system 10. The vent described with reference to FIGS. 29 through 30 closes upon actuation of the on/off valve 128.

Figure 31:
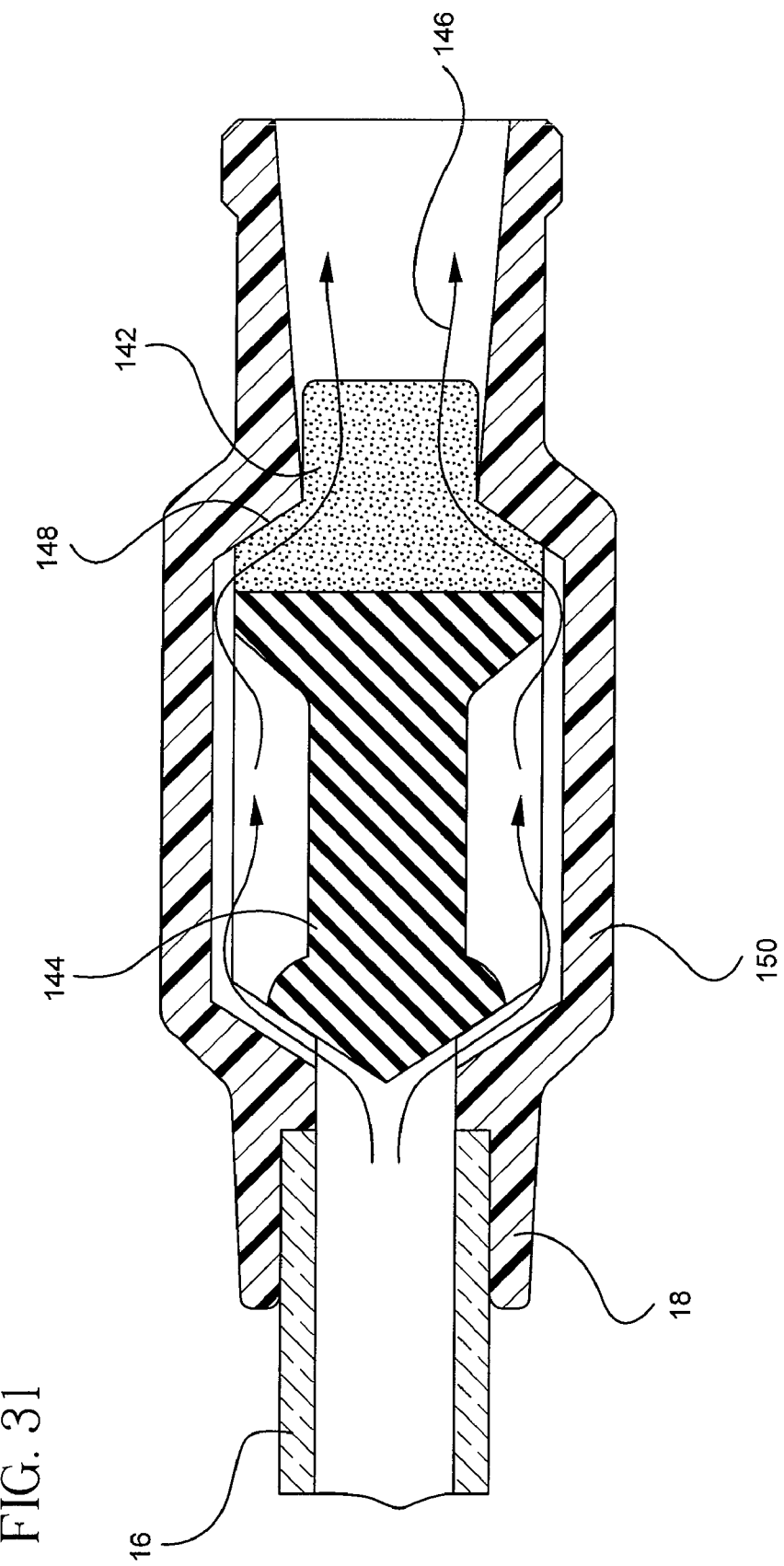
FIG. 31 is a cross section view of an adapter with a vent plug.

Referring now to FIG. 31, an adapter 18 includes a rigid and porous conical plug 142 housed within the internal lumen of the adapter 18. The plug 142 is displaced upon insertion of the tip of a Luer into the adapter 18. The rigid and porous conical plug 142 sits in communication with a return spring, such as an elastomeric return spring 144, also housed within the internal lumen of the adapter 18. Air or other gas is able to vent in a direction 146 through the adapter 18, past the spring 144, through the conical plug 142, and into the external atmosphere. The plug 142 sits against a taper 148 within the housing 150 of the adapter 18, permitting gas to escape through the plug 142 without permitting any fluid to escape through the porous conical plug 142.

Figure 32:
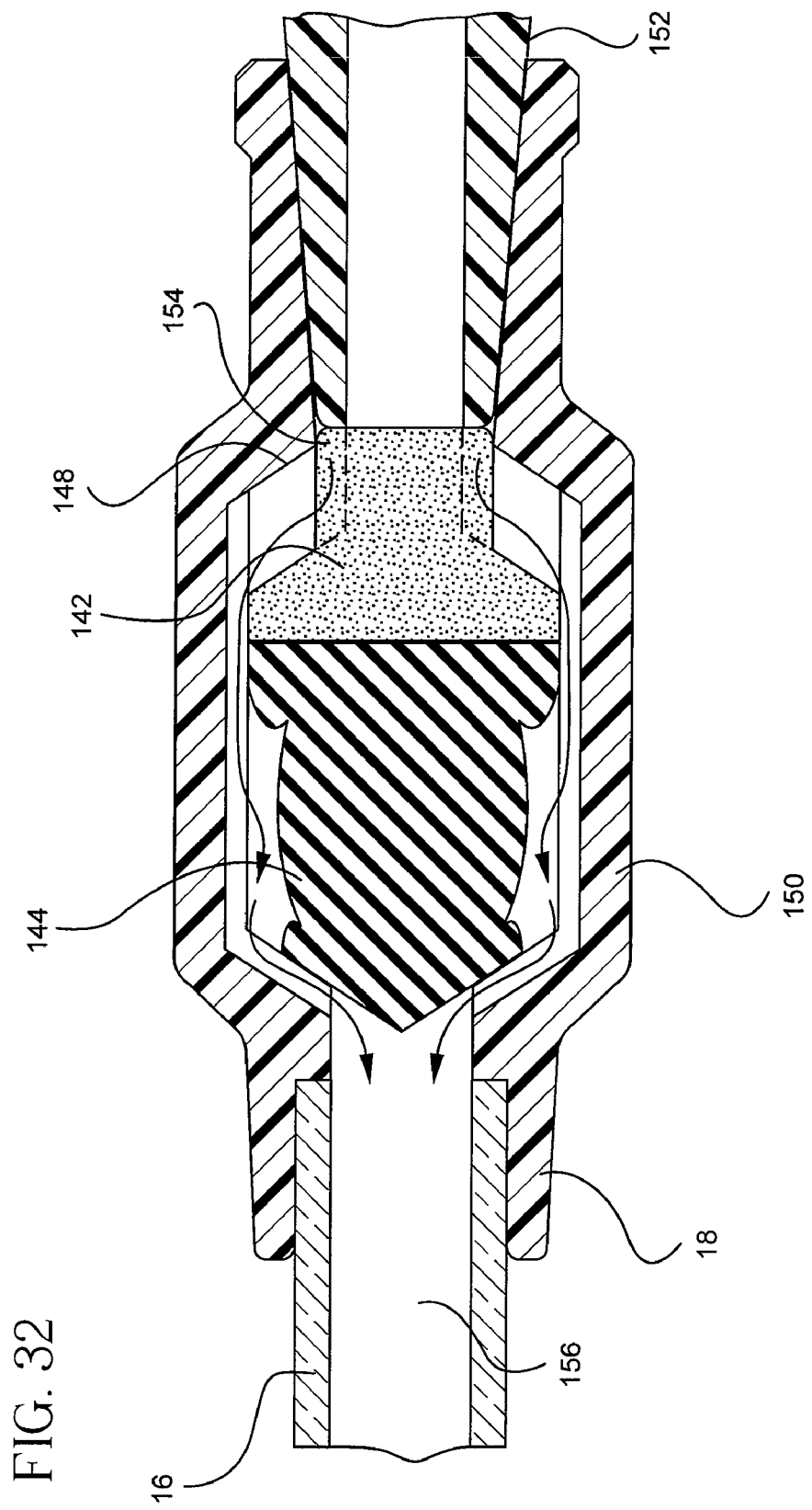
FIG. 32 is a cross section of the vent plug displaced within the adapter of FIG. 31.

Referring now to FIG. 32, the adapter 18 described with reference to FIG. 31 is shown with the male tip 152 of a Luer inserted into the adapter 18. The tip 152 displaces the plug 142, causing the plug 142 to be separated from the conical taper 148 as the return spring 144 is compressed, permitting fluid to be infused from the tip 152 into the adapter 18. The fluid is infused from the internal lumen of the tip 152 through air vents 154 formed within the plug 142, passed the plug 142 and spring 144 and into the downstream flow path 156 of an extravascular system 10. As the tip 152 is removed from the adapter 18, the spring 144 returns to its original position shown in FIG. 31, forcing the plug 142 to sit once again against the conical taper 148 of the housing 150 of the adapter 18.

Referring now to FIG. 33, an adapter 18 within an extravascular system 10 includes a vent 158 that closes upon actuation of a one-way ratcheting mechanism 160. The adapter 18 includes an upper portion 162 and a lower portion 164. The upper portion 162 is attached to the lower portion 164 by means of corresponding threads 166.

Referring now to FIG. 34, the embodiment described with reference to FIG. 33 is shown with the upper portion 162 fully screwed into the threads 166 of the lower portion 164. The one-way ratchet 160 prevents the upper portion 162 from unscrewing from the lower portion 164. In its fully closed position, the upper portion 162 seals the vent 158 from the internal cavity 168 of the adapter 18. The seal caused by the upper portion 162 in its closed position within the adapter 18 seals both the vent 158 and any blood that may need to be sealed from the fluid path of the internal cavity 168 during fluid infusion through the adapter 18. The one-way ratchet 160 is shown in FIG. 34A in cross section top view with the upper portion 162. The embodiments described with reference to FIG. 33, 34, and FIG. 34A thus describe a vent 158 that closes upon actuation of a one-way ratcheting mechanism 160.

Figure 35:
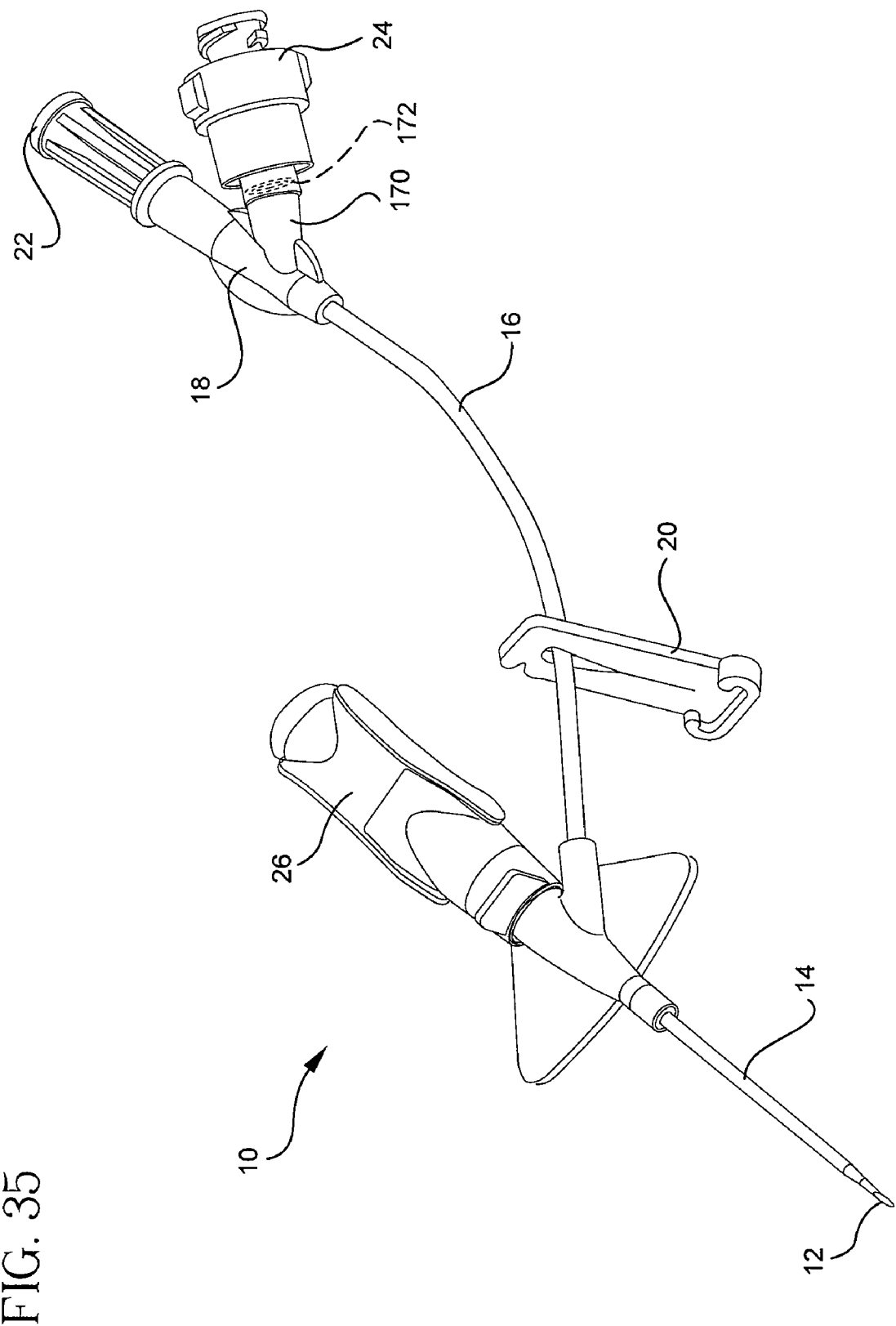
FIG. 35 is a perspective view of an extravascular system with an adapter having a hydrophobic ring.

Referring now to FIG. 35, an extravascular system 10 includes a vent 170 including a hydrophobic structure 172 such as a hydrophobic ring lined along the inner surface of the vent 170. The vent 170 forms part of a Y adapter 18 on a section to which a closed Luer access device 24 attaches. The diameter of the vent 170, which is a vent valve, is such that the diameter matches the diameter of the male Luer of the device 24. As the male Luer of the device 24 is inserted into the adapter 18, the hydrophobic structure 172 will flap down, hinging on one side within the vent 170, permitting the male Luer of the device 24 to pass by the hydrophobic ring 172. Thus, the embodiment described with reference to FIG. 35 provides a vent capable of repelling liquid as the system 10 vents gas through the vent 170. The hydrophobic ring 172 then will flap down and be removed from service upon attachment of a closed Luer access device 24 to the adapter 18.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
   a vascular access device, wherein the vascular access device forms part of an extravascular system and is an adapter for at least one other vascular access device;
   a vent cap removably fastened to a portion of the adapter, the vent cap including a septum and a cap body, the septum and cap body substantially forming a fluid and gas seal when the cap body is fastened to the adapter and the septum is in a closed position;
   a vent plug having an upper and a lower chamber, the lower chamber formed from at least one lower wall extending away from the upper chamber, the vent plug further having a cannula extending from the vent plug within the lower chamber, the lower chamber selectively mating with and substantially covering the vent cap when the cannula is inserted into the septum of the vent cap; and
   a gas permeable membrane forming a portion of the upper chamber of the vent plug.

2. The medical device of claim 1, wherein the at least one other vascular access device includes at least one catheter.

3. The medical device of claim 1, wherein the gas permeable membrane includes a microfiber material.

4. The medical device of claim 1, wherein the one or more wall of the lower chamber extends farther from the vent plug than the cannula.

5. The medical device of claim 1, wherein the inner surface of the one or more wall of the lower chamber of the vent plug includes one or more mating feature, and the outer surface of the vent cap include one or more mating feature that mate with one or more mating feature of the lower chamber of the vent plug when the vent plug mates with the vent cap.

6. A medical device, comprising:
   a vascular access device having a lumen and a lumen opening, wherein the vascular access device forms part of an extravascular system and is an adapter for at least one other vascular access device;
   a septum substantially sealing the lumen opening of the vascular access device when the septum is in a closed position;
   a vent plug having an upper chamber, a lower chamber, and a cannula;
   wherein the lower chamber is formed from at least one wall extending away from the upper chamber;
   wherein the cannula extends from the vent plug within the lower chamber;
   wherein the inner volume of the cannula is in fluid communication with the upper chamber;
   wherein the lower chamber has a geometry configured to selectively mate with and substantially cover the lumen opening and septum of the vascular access device when the cannula is inserted into the septum of the vascular access device; and
   a gas permeable membrane forming a portion of the upper chamber of the vent plug.

7. The medical device of claim 6, wherein the at least one wall of the lower chamber extends farther from the vent plug than the cannula.

* * * * *